(12) United States Patent
Kim et al.

(10) Patent No.: US 11,517,357 B2
(45) Date of Patent: Dec. 6, 2022

(54) COMBINATION SET SCREW BREAKOFF AND TAB BREAKER INSTRUMENT

(71) Applicant: Warsaw Orthopedic, Inc., Warsaw, IN (US)

(72) Inventors: Abel C. Kim, Cordova, TN (US); Mark R. Grizzard, Munford, TN (US); Gabriel H. Tonnessen, Memphis, TN (US); Richard Q. Brown, Collierville, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/166,466

(22) Filed: Feb. 3, 2021

(65) Prior Publication Data

US 2022/0240990 A1    Aug. 4, 2022

(51) Int. Cl.
*A61B 17/88* (2006.01)
*A61B 17/70* (2006.01)

(52) U.S. Cl.
CPC .............. *A61B 17/7091* (2013.01)

(58) Field of Classification Search
CPC ........... A61B 17/7091; A61B 17/7074; A61B 17/7076; A61B 17/7077; A61B 17/7079; A61B 17/708
USPC ................................................ 606/99, 86 A
See application file for complete search history.

(56) References Cited

U.S. PATENT DOCUMENTS

| | | | |
|---|---|---|---|
| 5,797,911 A | 8/1998 | Sherman et al. | |
| 7,625,394 B2 | 12/2009 | Molz, IV et al. | |
| 7,846,167 B2 | 12/2010 | Garcia et al. | |
| 7,846,767 B1 * | 12/2010 | Sung ................. | H01L 21/76256 438/105 |
| 7,914,559 B2 | 3/2011 | Carls et al. | |
| 7,967,821 B2 | 6/2011 | Sicvol et al. | |
| 8,016,836 B2 | 9/2011 | Corrao et al. | |
| 8,262,662 B2 | 9/2012 | Beardsley et al. | |
| 8,992,544 B2 | 3/2015 | Sasing | |
| 9,072,563 B2 | 7/2015 | Garcia et al. | |
| 9,186,138 B2 * | 11/2015 | Corradi ................. | B25B 23/101 |
| 9,402,673 B2 * | 8/2016 | Cormier ............ | A61B 17/8863 |
| 9,421,037 B2 * | 8/2016 | Harper ............... | A61B 17/7091 |
| 9,579,139 B2 | 2/2017 | Cormier et al. | |
| 9,668,784 B2 | 6/2017 | Brumfield et al. | |

(Continued)

*Primary Examiner* — Eduardo C Robert
*Assistant Examiner* — David C Comstock
(74) *Attorney, Agent, or Firm* — Fox Rothschild LLP; Paul Marshall Ticer

(57) ABSTRACT

A surgical system including a combination instrument for breaking of tabs of a reduction connector and providing a counter torque for a driver is disclosed. The combination instrument may have an elongated rigid structure and include an internal shaft and a magazine portion configured to store at least one tab of a reduction connector. The combination instrument may further include a cut-out portion configured to retain the at least one tab within the magazine portion. In some embodiments, the driver may be configured to be inserted into the internal shaft of the combination instrument. In some embodiments, the driver is rotatable within the internal shaft of the combination instrument and configured to drive a set screw within the reduction connector. Disclosed drivers may be manual drivers or powered drivers. Some embodiments, may include a collar or a cap from which the broken off tabs may be ejected.

8 Claims, 23 Drawing Sheets

(56) References Cited

U.S. PATENT DOCUMENTS

| | | | |
|---|---|---|---|
| 9,827,024 B2 | 11/2017 | Cormier et al. | |
| 9,943,342 B2 | 4/2018 | Tanaka et al. | |
| 9,968,394 B2 | 5/2018 | Meyer et al. | |
| 10,149,710 B2 | 12/2018 | Tanaka et al. | |
| 10,517,645 B2 | 12/2019 | van der Pol | |
| 10,531,903 B2 | 1/2020 | Daly et al. | |
| 10,555,729 B1 | 2/2020 | Cole et al. | |
| 10,561,411 B1 | 2/2020 | Cole et al. | |
| 10,603,078 B2 * | 3/2020 | Simpson | A61B 17/8869 |
| 10,743,858 B1 | 8/2020 | Cole et al. | |
| 10,806,498 B2 | 10/2020 | Erramilli et al. | |
| 11,090,097 B2 * | 8/2021 | Reed | A61B 17/8872 |
| 2004/0243139 A1 * | 12/2004 | Lewis | A61B 17/8891 |
| | | | 606/301 |
| 2008/0255576 A1 * | 10/2008 | Protopsaltis | A61B 17/7091 |
| | | | 227/176.1 |
| 2009/0149889 A1 * | 6/2009 | Peterson | A61B 17/862 |
| | | | 606/305 |
| 2010/0312279 A1 * | 12/2010 | Gephart | A61B 17/7091 |
| | | | 606/279 |
| 2019/0069934 A1 * | 3/2019 | Mickiewicz | A61B 17/861 |
| 2020/0330137 A1 * | 10/2020 | Rezach | F16B 23/0069 |
| 2021/0220023 A1 * | 7/2021 | Glaser | A61B 17/8872 |
| 2022/0022925 A1 | 1/2022 | Stoll et al. | |

\* cited by examiner

COMBINATION SET SCREW BREAKOFF AND TAB BREAKER INSTRUMENT

CROSS REFERENCE TO CO-RELATED APPLICATIONS

This application incorporates the disclosure of each of U.S. patent application Ser. No. 16,391,264, titled, INTERNAL BREAKOFF SET SCREW AND DRIVER, and U.S. Pat. No. 5,797,911, titled, MULTI-AXIAL BONE SCREW ASSEMBLY, by reference in its entirety.

BACKGROUND

Certain surgeons may prefer to use breakoff set screws when performing a reduction surgery such as fastening a rod to a connector of a spinal implant. Breakoff set screws may be preferred, for example, to avoid under and over torqueing the set screw, stripping the set screw, breaking the set screw, etc. Breakoff set screws may be, for example, external hex or hexalobular breakoff set screws. An example of a multi-axial screw including a breakoff screw is set forth in U.S. Pat. No. 5,797,911, which is incorporated herein by reference in its entirety.

Additionally, some surgeons may prefer to use a two part reduction connector to facilitate positioning of a rod within a passageway of the connector. A two part reduction connector may afford the surgeon greater freedom of movement of the rod during initial positioning of the rod due to its relatively large height, for example. In conventional practice, a surgeon often needs several distinct tools to break off a set screw, to tighten a set screw, and to break off the tabs of the connector. Requiring multiple tools can be cumbersome, increase the total surgery time, and increase the likelihood of introducing germs and viruses to the patient.

SUMMARY

The present disclosure relates generally to spinal stabilization systems, and more particularly, to surgical instruments for spinal stabilization systems. Disclosed instruments may be used to break off set screws, break off tabs of reduction connectors, and may store the broken off tabs within a cavity or magazine portion of the instrument, for example. Additionally, disclosed instruments may be configured to receive a driver for tightening of the set screw while also providing a counter torque for the connector and construct. Furthermore, disclosed drivers may be powered or manually operated.

In one aspect, the disclosure provides a surgical system, including a combination instrument. The combination instrument may have an elongated rigid structure extending from a proximal end to a distal end. The combination instrument may include a centrally disposed internal shaft extending from the proximal end to the distal end, and a magazine portion surrounding at least some of the internal shaft, for example. The magazine portion may be configured to selectively store at least one tab of a reduction connector. The combination instrument may further include a cut-out portion configured to retain the at least one tab within the magazine portion at the distal end, for example. The surgical system may further include a driver that is configured to be selectively inserted into the internal shaft of the combination instrument and selectively removed from the internal shaft of the combination instrument, for example. In various embodiments the distal end of the combination instrument is configured to surround a reduction connector, for breaking off tabs of the reduction connector in operation of the system, and the driver is rotatable within the internal shaft of the combination instrument and includes a drive interface configured to drive a set screw corresponding in size and shape to a size and shape of the drive interface.

In another aspect, the disclosure provides for a handle positioned on a side surface of the combination instrument that is configured to provide a counter torque to the reduction connector when driving the set screw in operation of the system, for example.

In another aspect, the disclosure provides for a magazine portion that is configured to selectively store a plurality of stacked broken off tabs, for example.

In another aspect, the disclosure provides that the combination instrument further includes a cap that is disposed at a proximal end of the combination instrument, for example. The cap may be configured to selectively retain the plurality of broken off tabs within the magazine portion at the proximal end of the combination instrument such that when the cap is removed the plurality of broken off tabs may exit the magazine portion at the proximal end of the combination instrument. Additionally, in some embodiments, the driver is insertable through an aperture in the cap exposing the internal shaft, for example.

In another aspect, the disclosure provides that the combination instrument further includes a collar. The collar may include at least two pins extending through corresponding channels of the combination instrument corresponding in size and shape to a size and shape of the at least two pins, respectively, for mating with the at least two pins, for example. In various embodiments, the at least two pins may extend into the magazine portion, for example. In some embodiments, the collar may be configured to slide along an outside surface of the combination instrument towards a distal end of the combination instrument to selectively eject the at least one tab stored in the magazine portion from the distal end of the combination instrument.

In another aspect, the disclosure provides that the driver is configured to be driven by a powered device, for example.

In another aspect, the disclosure provides that the driver comprises at least one ball and a corresponding biasing spring disposed on a drive portion of the driver, for example. In some embodiments, the at least one ball and corresponding biasing spring may be configured to apply a lateral force against internal sidewalls of a head portion of the set screw.

In another aspect, the disclosure provides that the set screw may be a breakoff set screw, and the driver may be configured to break off a breakoff portion of the set screw, for example. In various embodiments, the at least one ball and corresponding biasing spring may be configured to retain the breakoff portion of the breakoff set screw, for example.

In one aspect, the present disclosure provides for a combination instrument. The combination instrument may include an elongated rigid structure extending in a longitudinal direction from a proximal end to a distal end, and the elongated rigid structure may include an outside surface and an inside surface opposite the outside surface, for example. The combination instrument may include an internal shaft that is centrally disposed relative to the elongated rigid structure and extending in the longitudinal direction from the proximal end of the elongated structure towards the distal end of the elongated structure, for example. The combination instrument may further include a magazine portion that extends in the longitudinal direction and is disposed between the inside surface and the internal shaft, for example. The combination instrument may further include a cut-out portion, the cut-out portion may be disposed on the outside surface of the distal end of the elongated rigid structure, for example. In some embodiments, the cut-out portion may be configured to retain the at least one tab within the magazine portion at the distal end. Additionally, in various embodiments, the internal shaft may be configured to selectively receive a driver such that the driver may freely rotate within the internal shaft, and the combination instrument may be configured to surround a reduction connector, at least in part, for breaking off tabs of the reduction connector, for example. In various embodiments, the magazine portion may be configured to selectively store at least one broken off tab of a reduction connector, at least temporarily.

In another aspect, the disclosure provides that a handle may be positioned on a side surface of the elongated rigid structure, and the handle may be configured to provide a counter torque, for example.

In another aspect, the disclosure provides that the magazine portion may be configured to selectively store a plurality of stacked broken off tabs, for example.

In another aspect, the disclosure provides that a cap may be disposed at the proximal end of the elongated rigid structure, and the cap may be configured to selectively retain the plurality of broken off tabs within the magazine portion at the proximal end of the elongated rigid structure such that when the cap is removed the plurality of broken off tabs may exit the magazine portion at the proximal end of the elongated rigid structure, for example Additionally, the disclosure provides that a driver may be insertable through an aperture in the cap exposing the internal shaft, for example.

In another aspect, the disclosure provides that the elongated rigid structure may further include a collar, the collar including at least two pins extending through corresponding channels of the elongated rigid structure into the magazine portion, for example. In various embodiments, the corresponding channels may have a size and shape corresponding to size and shape of the at least two pins for mating with the at least two pins, respectively. Additionally, the disclosure provides that the collar may be configured to slide along the outside surface of the elongated rigid structure towards the distal end of the elongated rigid structure thereby selectively ejecting the at least one tab stored in the magazine portion from the distal end of the elongated rigid structure.

In another aspect, the disclosure provides that the drive shaft may be configured to receive a powered driver and the magazine portion may be configured to selectively store a plurality of broken off tabs, for example.

In another aspect, the disclosure provides that the elongated rigid structure may include a cap, and the cap may be disposed at the proximal end of the elongated rigid structure. In various embodiments, the cap may be configured to selectively retain the plurality of broken off tabs within the magazine portion at the proximal end of the elongated rigid structure such that when the cap is removed the plurality of broken off tabs may exit the magazine portion at the proximal end of the elongated rigid structure, and the powered driver may be insertable through an aperture in the cap exposing the internal shaft, for example.

In another aspect, the disclosure provides that the elongated rigid structure may include a collar, and the collar may include at least two pins extending through corresponding channels of the elongated rigid structure into the magazine portion, for example. In various embodiments, the corresponding channels may have a size and shape corresponding to size and shape of the at least two pins for mating with the at least two pins, respectively. In various embodiments, the collar may be configured to slide along the outside surface of the elongated rigid structure towards the distal end of the elongated rigid structure to selectively eject the at least one tab stored in the magazine portion from the distal end of the elongated rigid structure, for example.

In another aspect, the disclosure provides for a method of breaking off a plurality of tabs of a reduction connector, for example. The method may include the step of providing a combination instrument. In various embodiments, the combination instrument may include an elongated rigid structure extending in a longitudinal direction from a proximal end to a distal end, and the elongated rigid structure may include an outside surface, for example. In various embodiments, an internal shaft may be centrally disposed relative to the elongated rigid structure and extend in the longitudinal direction from the proximal end of the elongated structure towards the distal end of the elongated structure, for example. In various embodiments, a magazine portion may extend in the longitudinal direction and be disposed between the elongated rigid structure and the internal shaft, for example. In various embodiments, a cut-out portion may be disposed on the outside surface of the distal end of the elongated rigid structure, and the cut-out portion may be configured to retain the at least one tab within the magazine portion, for example. In various embodiments, the step of positioning a tip portion of the combination instrument at an elevation corresponding to a break off portion of the reduction connector may be performed, for example. Additionally, the step of moving the combination instrument laterally to break off at least one tab of the reduction connector, may be performed, for example. Furthermore, the step of ejecting the at least one tab from the magazine portion of the combination instrument from either the distal side of the elongated rigid structure or the proximal side of the elongated rigid structure may be performed, for example.

BRIEF DESCRIPTION OF DRAWINGS

The following drawings are illustrative of particular embodiments of the present disclosure and therefore do not limit the scope of the present disclosure. The drawings are not to scale and are intended for use in conjunction with the explanations in the following detailed description.

DETAILED DESCRIPTION

Figure 1:
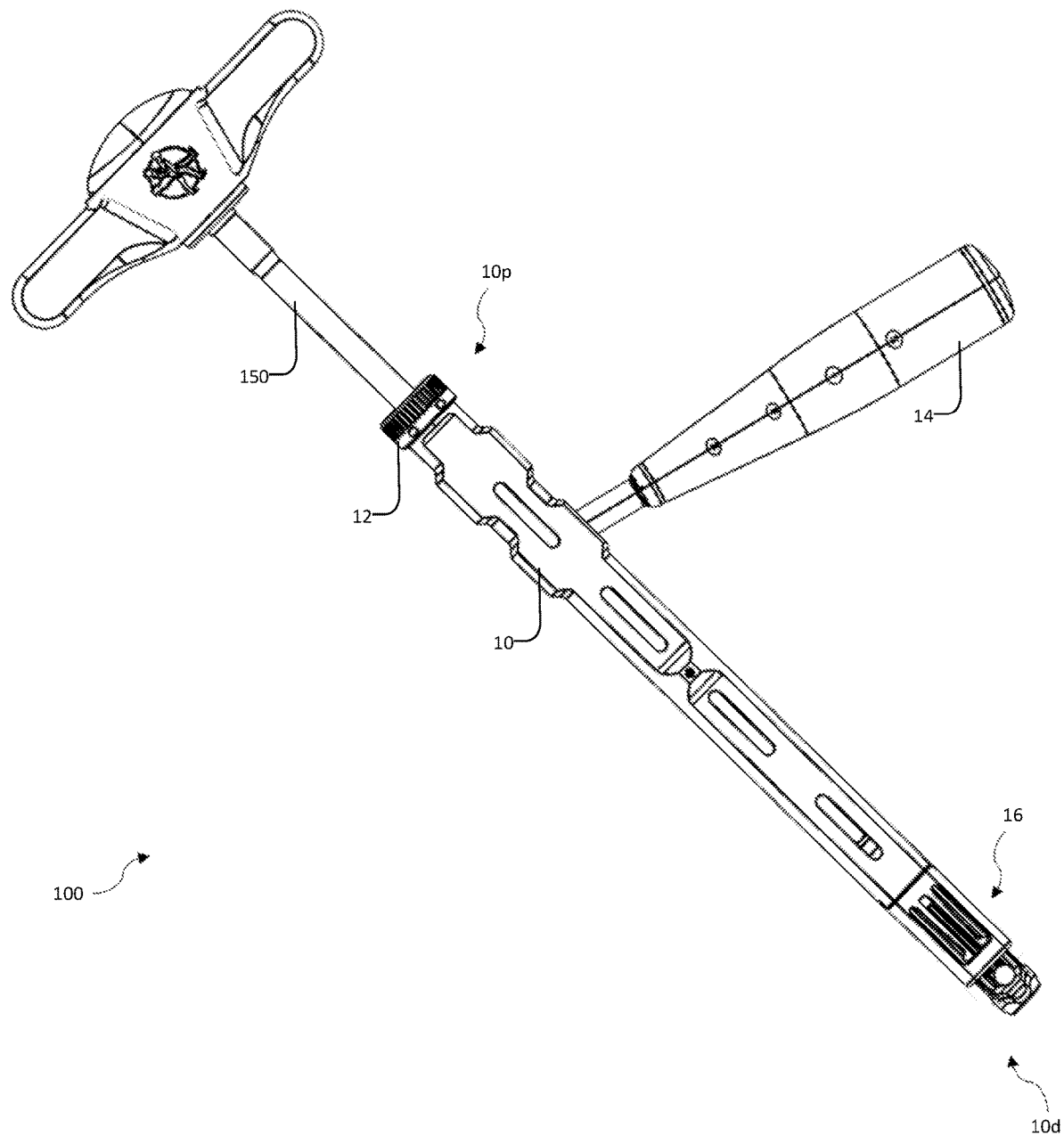
FIG. 1 is an example side perspective view of a combination instrument and a driver.
Figure 2A:
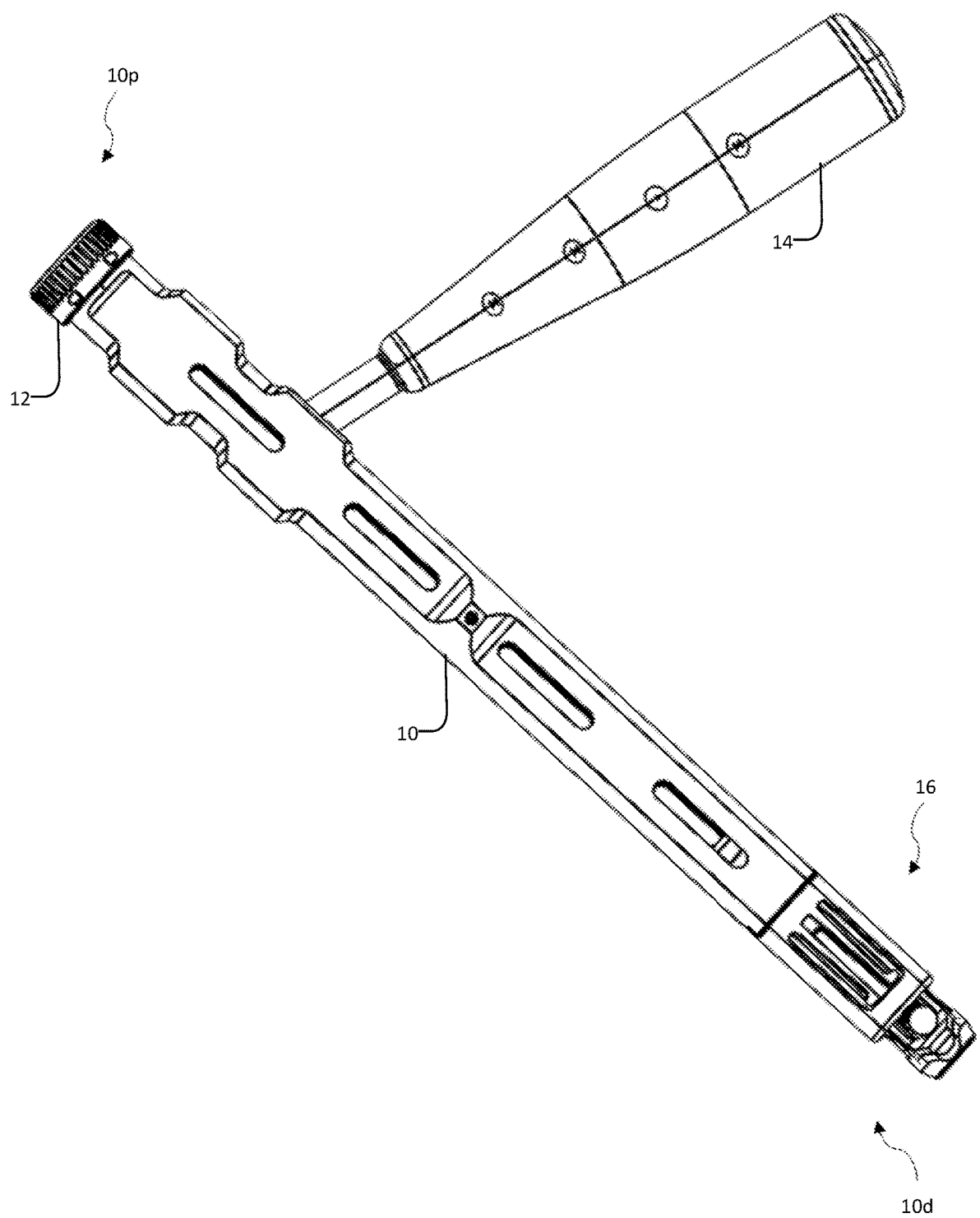
FIG. 2A is an example side perspective view of a combination instrument.
Figure 2B:
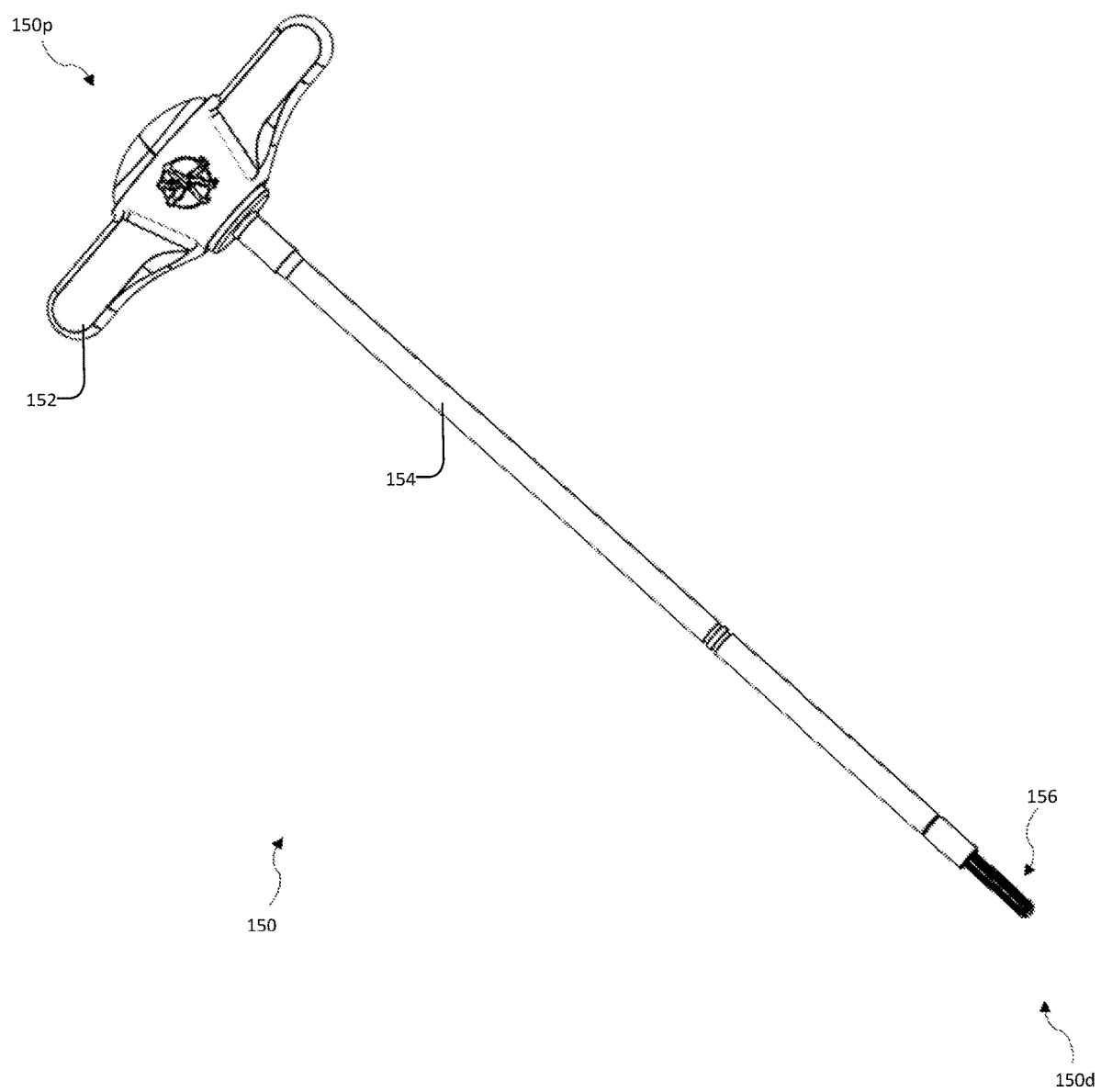
FIG. 2B is an example side perspective view of a manual driver.

The following discussion omits or only briefly describes certain components, features and functionality related to spinal stabilization systems, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are example concepts of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context clearly indicates otherwise.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally, for example, to spinal stabilization systems, and more particularly, to surgical instruments for spinal stabilization systems. Embodiments of the devices and methods are described below with reference to the Figures.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Referring generally to FIGS. 1-11, a surgery system 100 including a combination instrument 10 and a manual driver 150 is disclosed. FIG. 1 is an example side perspective view of a surgery system 100 including a combination instrument 10 and a manual driver 150. FIG. 2A is an example side perspective view of a combination instrument 10 and FIG. 2B is an example side perspective view of a manual driver 150.

Combination instrument 10 may include a distal end 10*d* and a proximal end 10*p*. The proximal end 10*p* may include a cap 12, such as a twist off cap for example, and the distal end 10*d* may include a cut-out portion 16. Combination instrument 10 may include a handle 14, for example. Handle 14 may be configured for use as a counter torque handle and/or as a positioning handle, for example. Combination instrument 10 may be configured to break off tabs of a reduction connector, as will be explained in further detail below.

Manual driver 150 may include a handle 152 disposed at a proximal side 150*p* and a drive portion 156 disposed at a distal side 150*d*, for example. In the example surgery system 100, combination instrument 10 may include an interior shaft configured to receive manual driver 150. For example, manual driver 150 may be inserted through an aperture in cap 12 at the proximal end 10*p* that exposes an interior shaft of the combination instrument 10 such that the manual driver 150 may extend through the interior shaft of combination instrument 10 towards a distal end 10*d* of combination instrument 10. The drive shaft 154 of manual driver 150 may extend through an interior shaft of combination instrument 10 and freely rotate inside of combination instrument 10 when the magazine portion 15 is stacked with broken off tabs 3*c* and 3*d*, for example. For example still, the driver 150 may be rotatable within an internal shaft of the combination instrument and include a drive interface that corresponds in size and shape to size and shape of the head of a corresponding reduction set screw 2 such that the driver 150 may drive the reduction set screw 2 within a reduction connector 3.

Figure 3:
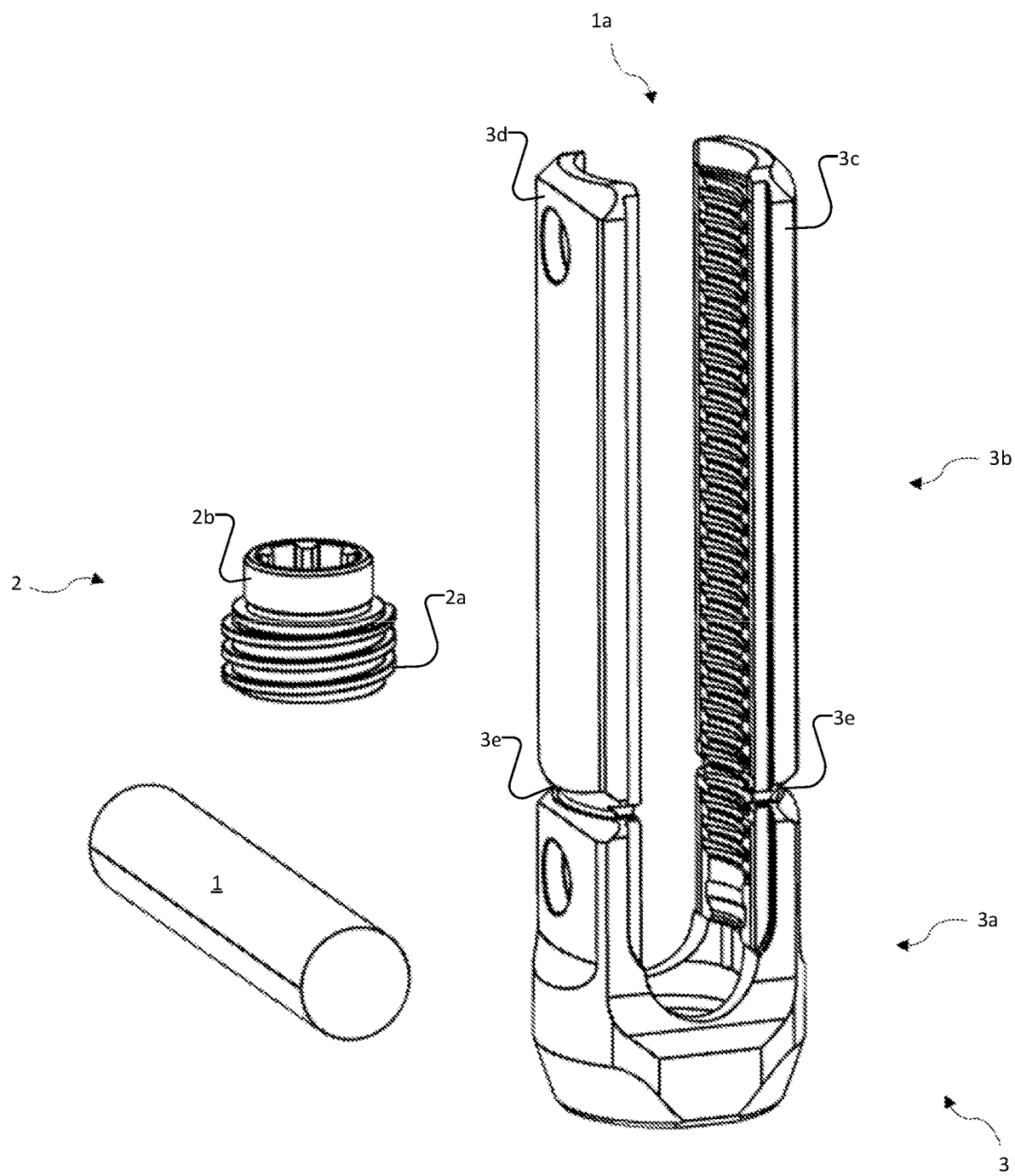
FIG. 3 is an example exploded parts view of a rod, a reduction screw, and a reduction connector.
Figure 4:
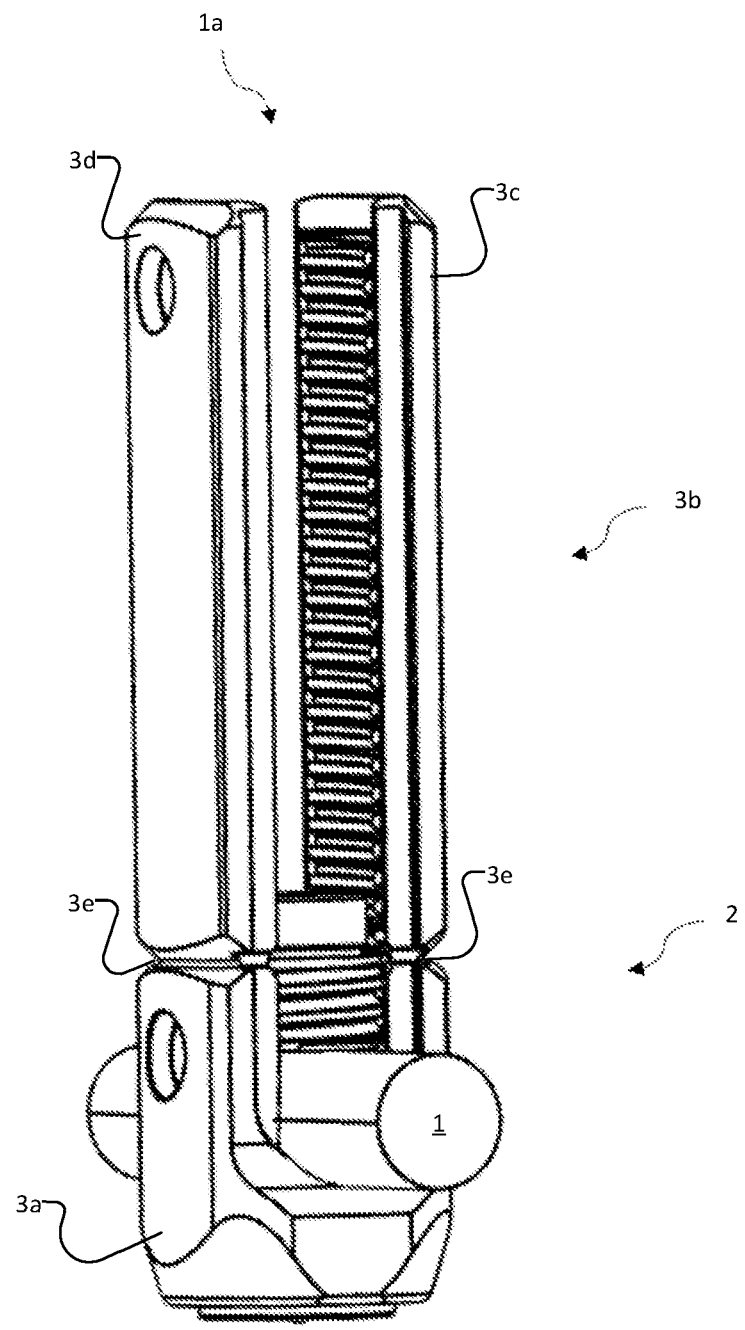
FIG. 4 is an assembled parts view of a rod, a reduction set screw, and a reduction connector.

FIG. 3 is an example exploded parts view of a rod 1, a reduction set screw 2, and a reduction connector 3. FIG. 4 is an assembled parts view of a rod 1, a reduction set screw 2, and a reduction connector 3. Reduction set screw 2 may include a bottom portion 2*a* and a top portion 2*b*, for example. The top portion 2*b* may be configured to be broken off of the bottom portion 2a, as will be explained in further detail below. In some embodiments, top portion 2b may include a groove within the drive interface portion. Reduction set screw 2 may be configured to be driven by manual driver 150 and include a hexalobular drive interface, for example.

In the example embodiment, reduction connector 3 may include a rod passageway 1a configured to receive rod 1 therein. The example reduction connector 3 may include an internal thread pattern configured to engage with a corresponding thread pattern of reduction set screw 2, for example. The example reduction connector 3 may include a bottom portion 3a and a top portion 3b, for example. The top portion 3b may be configured to be broken off of the bottom portion 3a, as will be explained in further detail below. For example, the top portion may include a pair of tabs 3c and 3d that adjoin bottom portion 3a at a breakoff location 3e, for example. Breakoff location 3e may be a portion of reduction connector 3 having a relative thickness that is less than the relative thickness of the immediately adjacent portions of reduction connector 3, for example. This configuration may facilitate the break off tabs 3c and 3d from separating from reduction connector 3 due to an applied shear force, for example.

Figure 5:
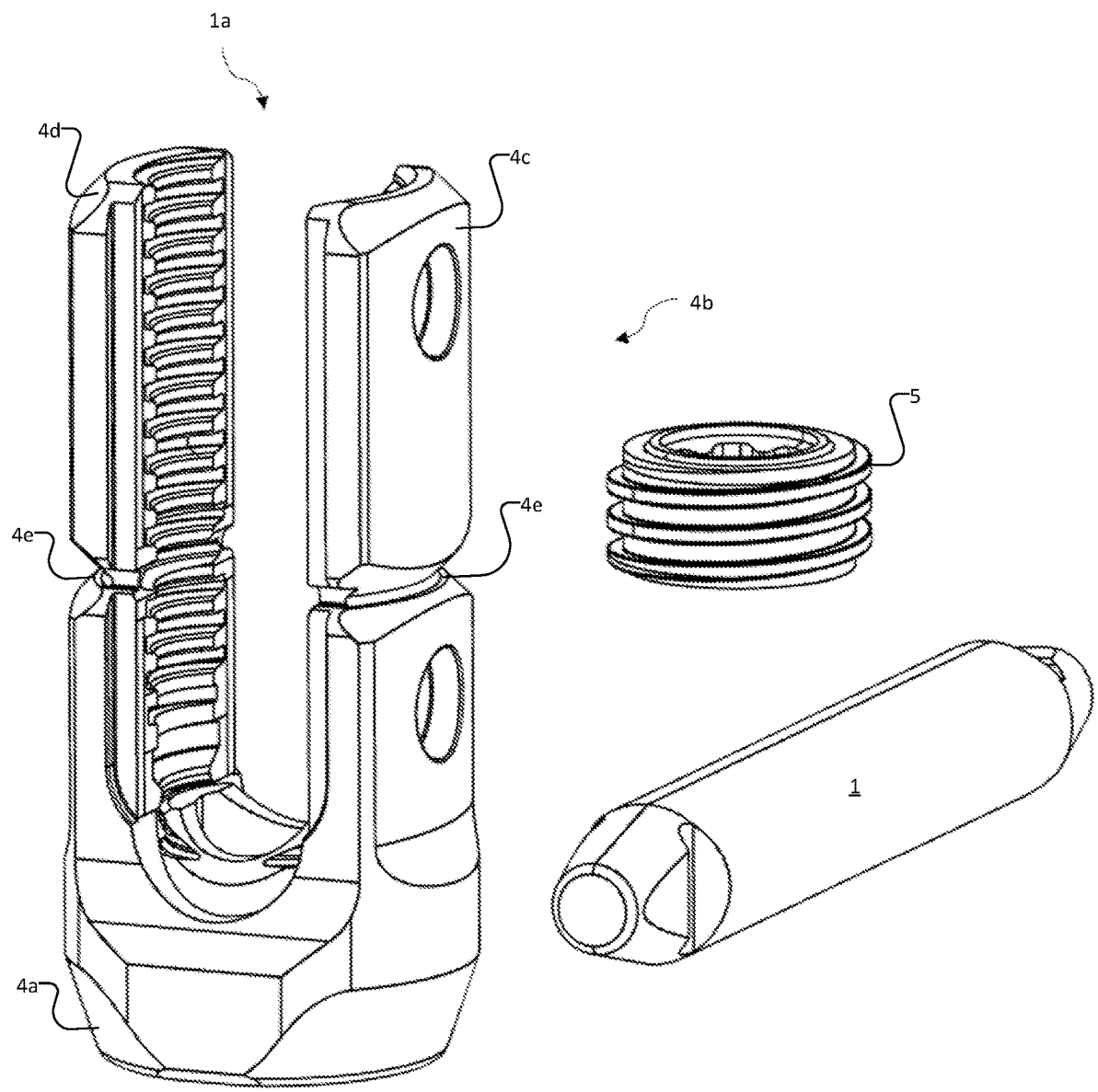
FIG. 5 is an example exploded parts view of a rod, a non-reduction set screw, and a reduction connector.
Figure 6:
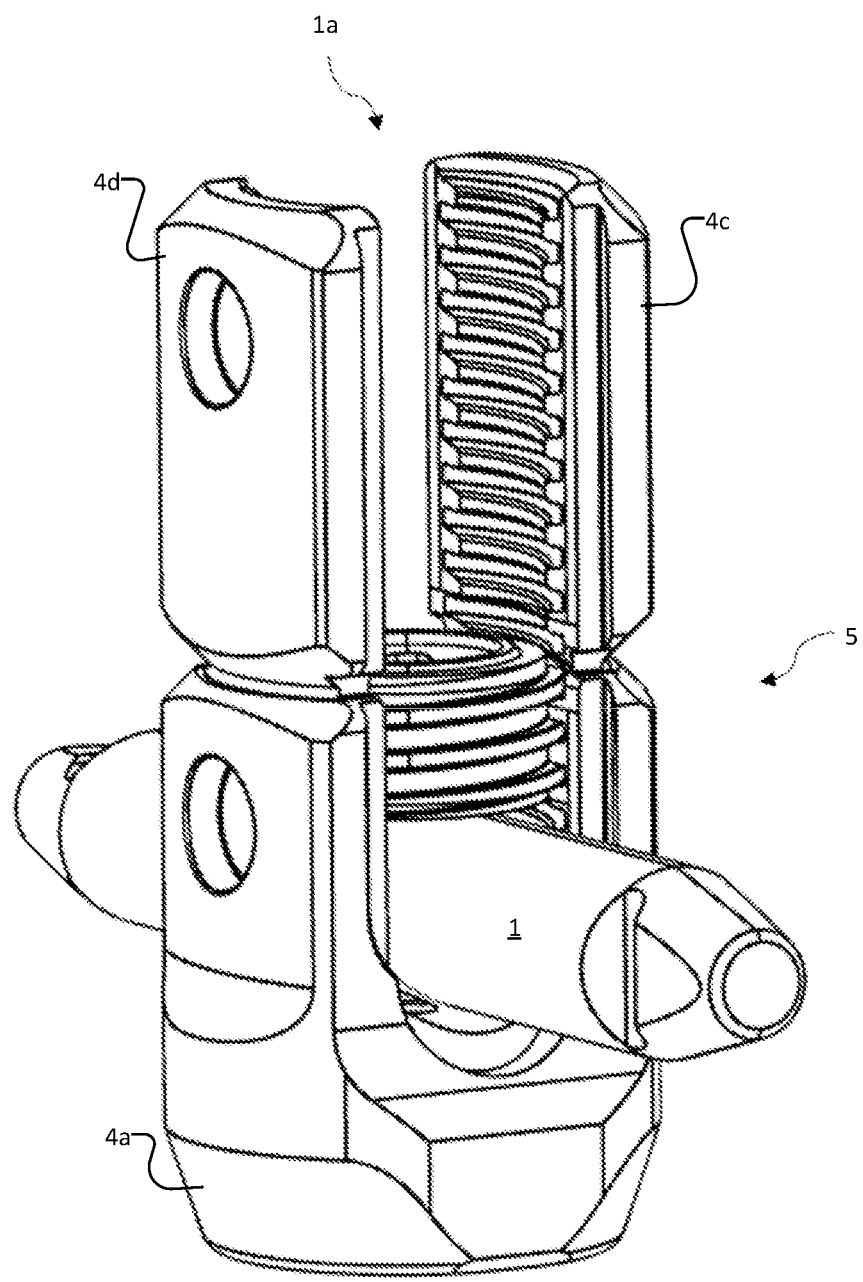
FIG. 6 is an assembled parts view of a rod, a non-reduction set screw, and a reduction connector.

FIG. 5 is an example exploded parts view of a rod 1, a non-reduction set screw 5, and a reduction connector 4. FIG. 6 is an assembled parts view of a rod 1, a non-reduction set screw 5, and a reduction connector 4. In the example embodiment, non-reduction set screw 5 may differ from reduction set screw 2 in that it may not include a top portion configured to be broken off. However, non-reduction set screw 5 may still be configured to fix rod 1 relative to connector 4. In the example embodiment, reduction connector 4 may differ from reduction connector 3 in that reduction connector 4 is relatively shorter in height than reduction connector 3. However, both reduction connectors 3 and 4 may functionally and structurally correspond to one another. For example, reduction connector 4 may also include an internal thread pattern configured to engage with a corresponding thread pattern of either set screw 2 or 5 for example. The example reduction connector 4 may include a bottom portion 4a and a top portion 4b, for example. The top portion 4b may be configured to be broken off of the bottom portion 4a, as will be explained in further detail below. For example, the top portion may include a pair of tabs 4c and 4d that adjoin bottom portion 4a at a breakoff location 4e.

Figure 7:
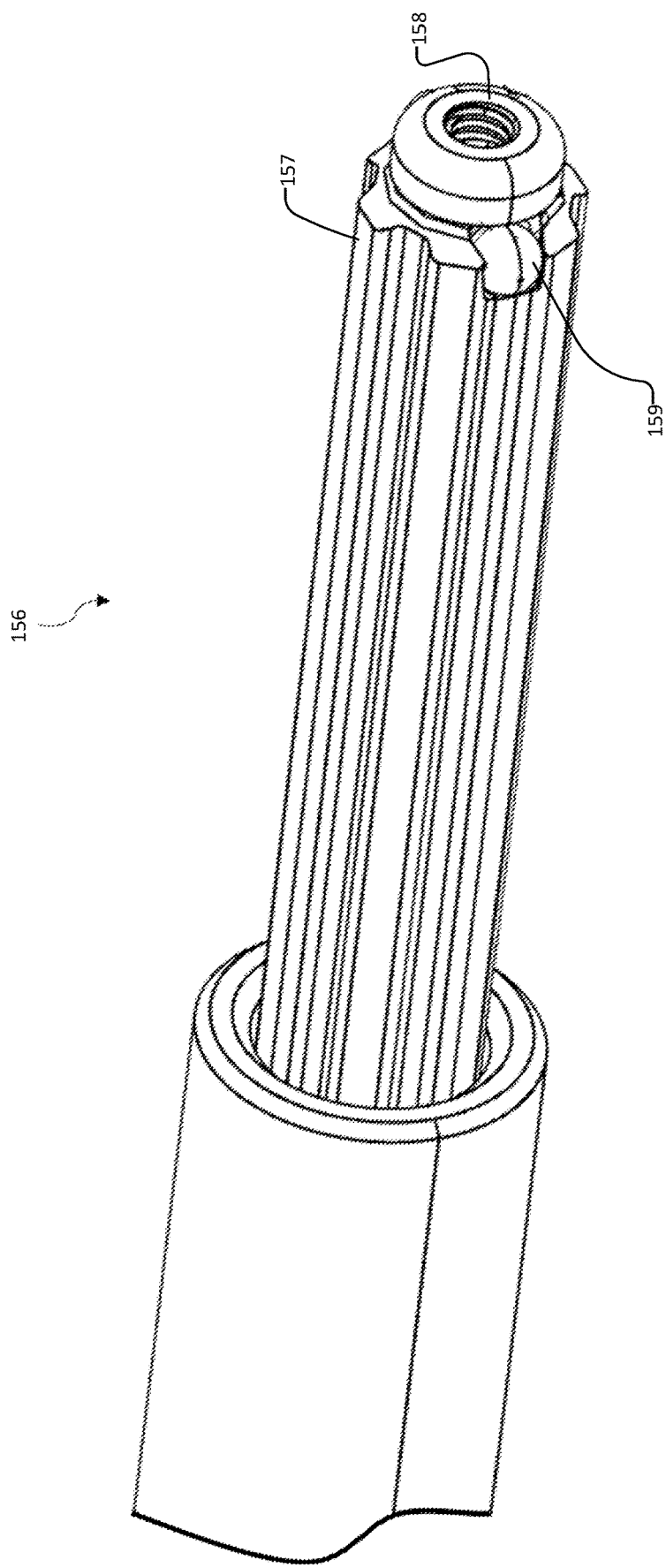
FIG. 7 is an example perspective view of a drive portion of a manual driver.

FIG. 7 is an example perspective view of a drive portion 156 of a manual driver 150. Drive portion 156 may include a hexalobular drive interface 157 and be configured to drive a corresponding set screw 2 and/or 5 for example. However, other embodiments may use other interfaces, for example, a torx driver, hex driver, phillips driver, square head driver, hexalobular driver, polygonal driver, or the like. Drive portion 156 of manual driver 150 may further include a ball portion 159 and an internal thread portion 158 disposed at a tip thereof. The ball portion 159 may be configured to facilitate the retention of a set screw 2 thereon, as will be explained in further detail below.

Figure 8:
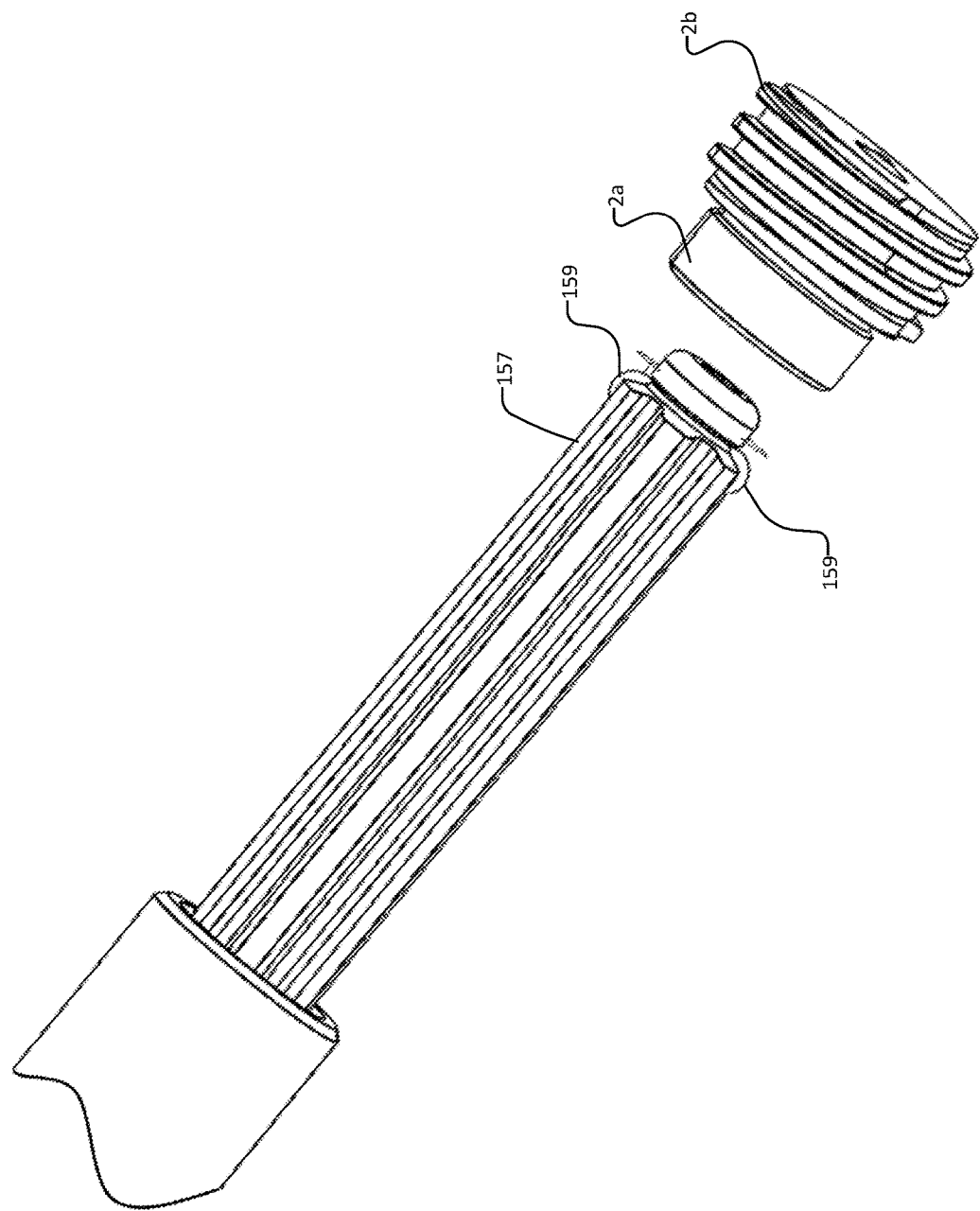
FIG. 8 is an example perspective view of a drive portion of a manual driver before being inserted into a reduction screw.
Figure 9:
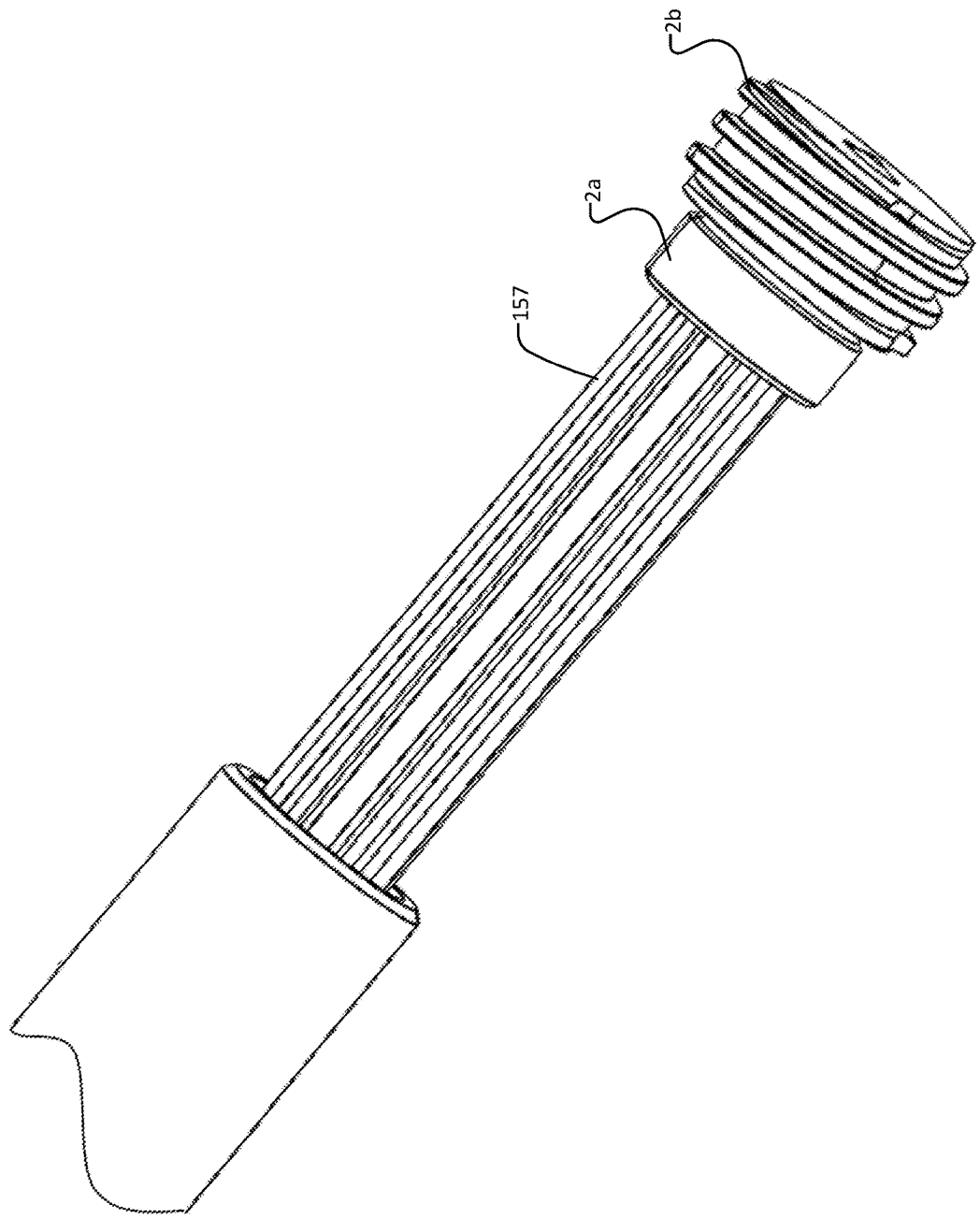
FIG. 9 is an example perspective view of a drive portion of a manual driver after being inserted into a reduction screw.
Figure 10:
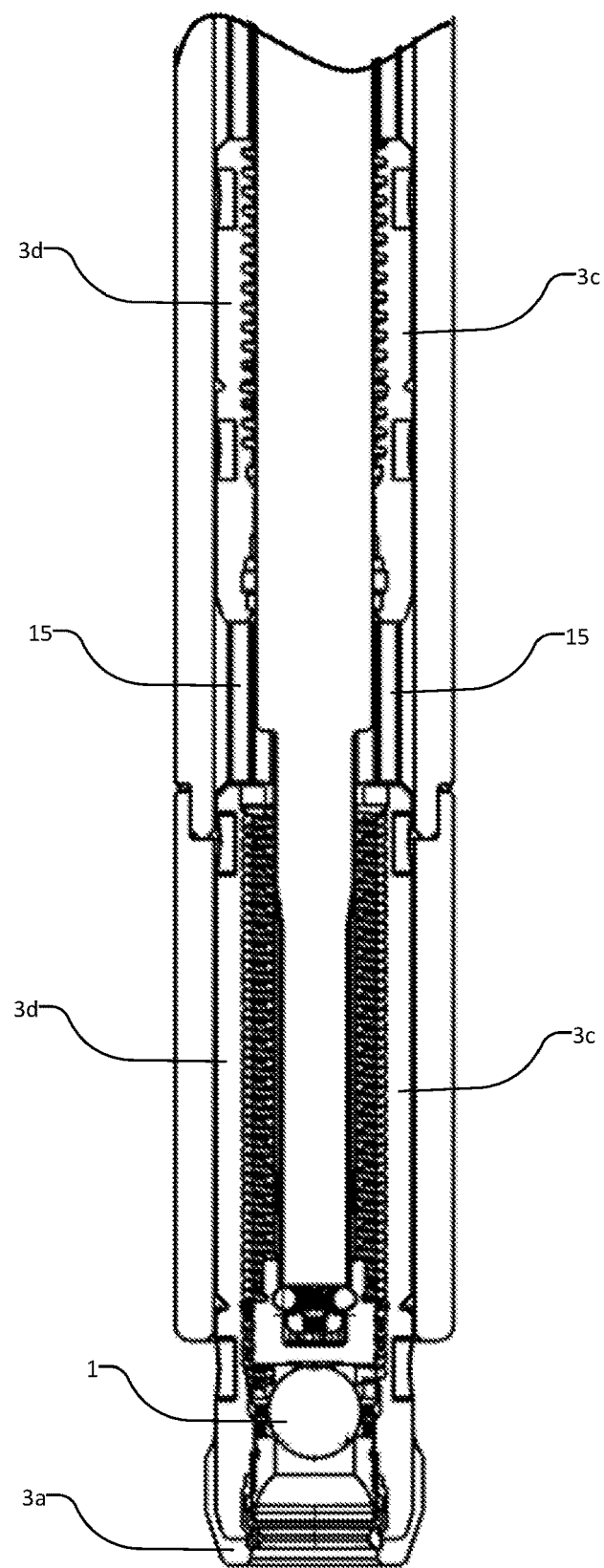
FIG. 10 is an example cross section view of a combination instrument and manual driver seated on a reduction connector and reduction screw.
Figure 11:
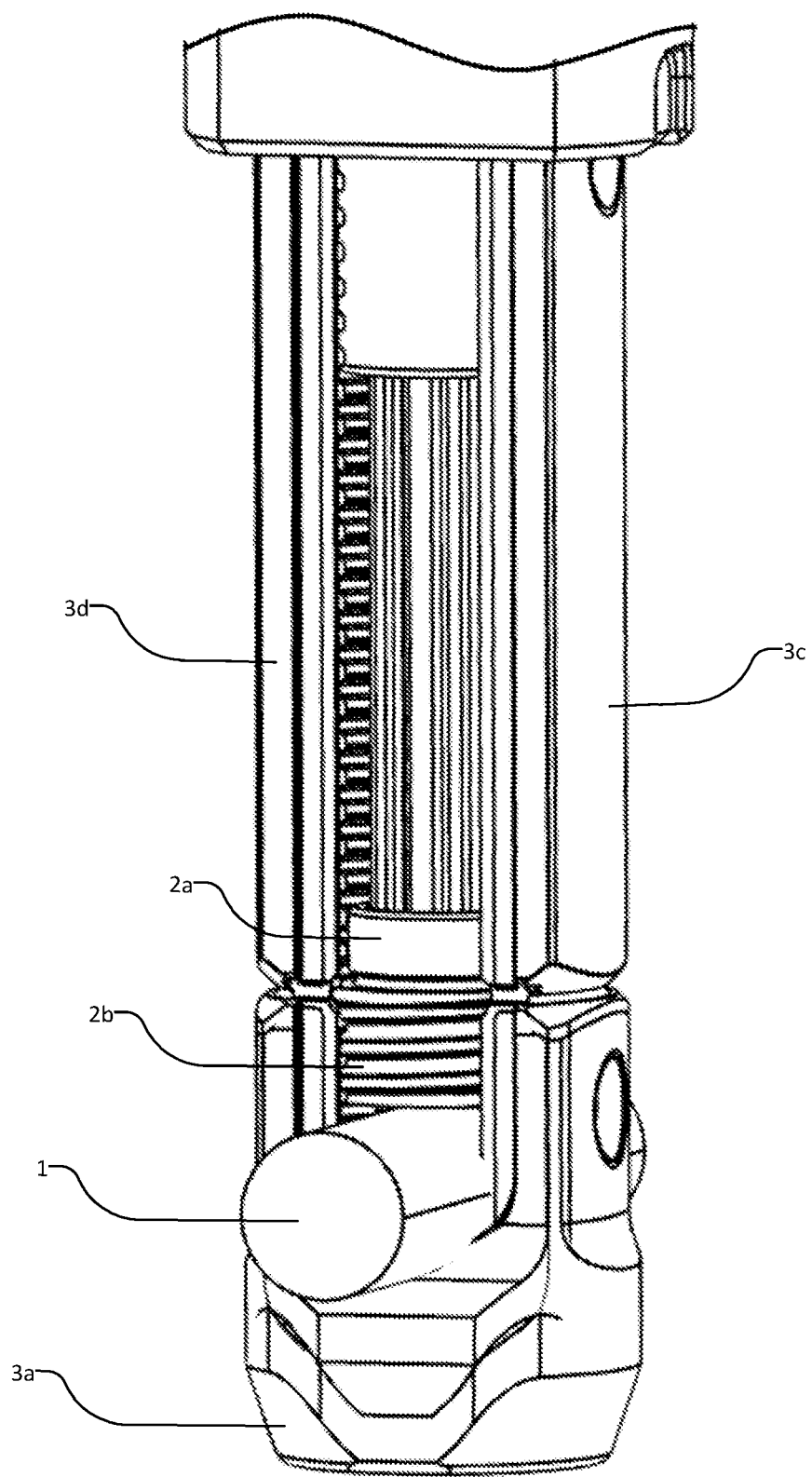
FIG. 11 is an example perspective view of a combination instrument and manual driver seated on a reduction connector and reduction screw.

FIG. 8 is an example perspective view of a drive portion 156 of a manual driver 150 before being inserted into a reduction set screw 2. FIG. 9 is an example perspective view of a drive portion 156 of a manual driver 150 after being inserted into a reduction set screw 2. FIG. 10 is an example cross section view of a combination instrument 10 seated on a reduction connector 3 and a manual driver 150 mated with a reduction set screw 2. FIG. 11 is an example perspective view of a manual driver 150 seated on a reduction set screw 2. In the example embodiment, a distal end of combination instrument 10 is inserted over the top portion 3b of reduction connector 3, for example. The drive portion 156 including the drive interface 157 and a pair of balls 159 may be seated within a head portion of set screw 2, for example. In the example embodiment, the balls 159 may be coupled to a biasing spring 159. In some embodiments, the set screw 2 and/or 5 may have a groove in the drive cavity of the head thereof that corresponds in size, shape, and location to size, shape, and location of the balls 159, for example. The biasing spring may be configured to naturally urge the balls 159 laterally away from drive portion 156, for example. In the illustrated embodiment, the balls 159 are illustrated as applying a lateral force against the internal sidewalls of the head portion of set screw 2, for example. At least one advantage of this arrangement is that the balls 159 apply a retaining force against the inside of set screw 2. This retaining force may be advantageous for retaining set screw 2 relative to manual driver 150. Additionally, this retaining force may be advantageous for retaining the top portion 2b of set screw 2 after the top portion 2b has been sheared or broken off from bottom portion 2a.

In practice, a surgeon may use surgery system 100 with a reduction connector 3 for stabilization and/or correction of a patient's spine, for example. A surgeon may insert rod 1 into rod passageway 1a of reduction connector 3 and reduce the rod 1 by tightening set screw 2 towards a bottom portion of reduction connector 3. In some embodiments, the surgeon may break off the top portion of reduction set screw 2 by moving the manual driver 150, or a similar break off driver (not illustrated), laterally from the medial position, for example. A surgeon may grasp handle 14 and utilize combination instrument 10 as a counter torque for fully tightening of set screw 2 relative to connector 3, for example. Additionally, the surgeon may position the combination instrument 10 such that a tip of the distal end 10d is aligned at the same elevation as the breakoff portion 3e of reduction connector 3. In some embodiments, a surgeon may retract the drive end of driver 150 towards a proximal side 10p of combination instrument 10 to protect the tip of the drive end when rocking combination instrument 10. Alternatively, in some embodiments, a surgeon may remove driver 150 from combination instrument 10 to protect the tip of the drive end when rocking combination instrument 10. Once the combination instrument 10 is positioned at the proper elevation, a surgeon may grasp handle 14 and rock combination instrument 10 laterally from a medial position, for example. In doing so, the top portion 3b of reduction connector 3 may shear off or break off from the bottom portion 3a of reduction connector 3, for example. The broken off tabs 3d and 3c may be stored within an interior magazine portion 15 of combination instrument 10 that is configured to selectively store the broken off tabs 3d and 3c, at least temporarily. As used herein, the terms "selective" and "selectively" shall have their ordinary meaning that a described function and/or outcome may optionally occur. For example, the magazine portion 15 may selectively store broken off tabs 3c and 3d means that the magazine portion may optionally store tabs 3c and 3d that may also be removed, as will be explained in further detail below. For example still, the broken off tabs 3d and 3c may be stored and/or retained, at least temporarily, until such a time that an end user such as a surgeon completes a surgery, a portion of a surgery, and/or otherwise desires to remove them. Furthermore, the broken off tabs 3c and 3d may be kept from sliding down and out of distal end 10d due to the cut-out portion 16 being slightly inset from an outside surface of combination instrument 10. In various embodiments, the cut-out portion 16 may include ribs, cross pins, and/or flanges that are vertically aligned with rails of the magazine portion 15 such that broken off tabs 3c and 3d may not slide out. For example, as shown in FIG. 10, a pair of broken tabs 3c and 3d (top most tabs 3c and 3d) are from a previous reduction connector 3 and are stacked and retained within magazine portion 15. In this way, FIG. 10 illustrates one example of how a surgeon may quickly move freely between a plurality of reduction connectors 3 and/or 4 and the broken tabs 3c and 3d may sequentially slide up a magazine portion 15 towards the proximal end 10p of combination instrument 10. For example, broken tabs 3c and 3d may slide up a rail that corresponds in size and shape to the geometry of the broken tabs 3c and 3d. After the surgeon has finished reducing the desired number of reduction connectors 3 and/or 4 the surgeon may remove the reduction connectors 3 and/or 4. For example, the surgeon may empty the reduction connectors 3 and/or 4 that are stacked in the magazine portion 15 when the magazine portion is full of broken tabs 3c and 3d or the desired amount of reduction connectors 3 and/or 4 have been reduced. The surgeon may twist off the cap 12 and empty the broken tabs 3c and 3d through the proximal end 10p of combination instrument, for example.

Figure 12:
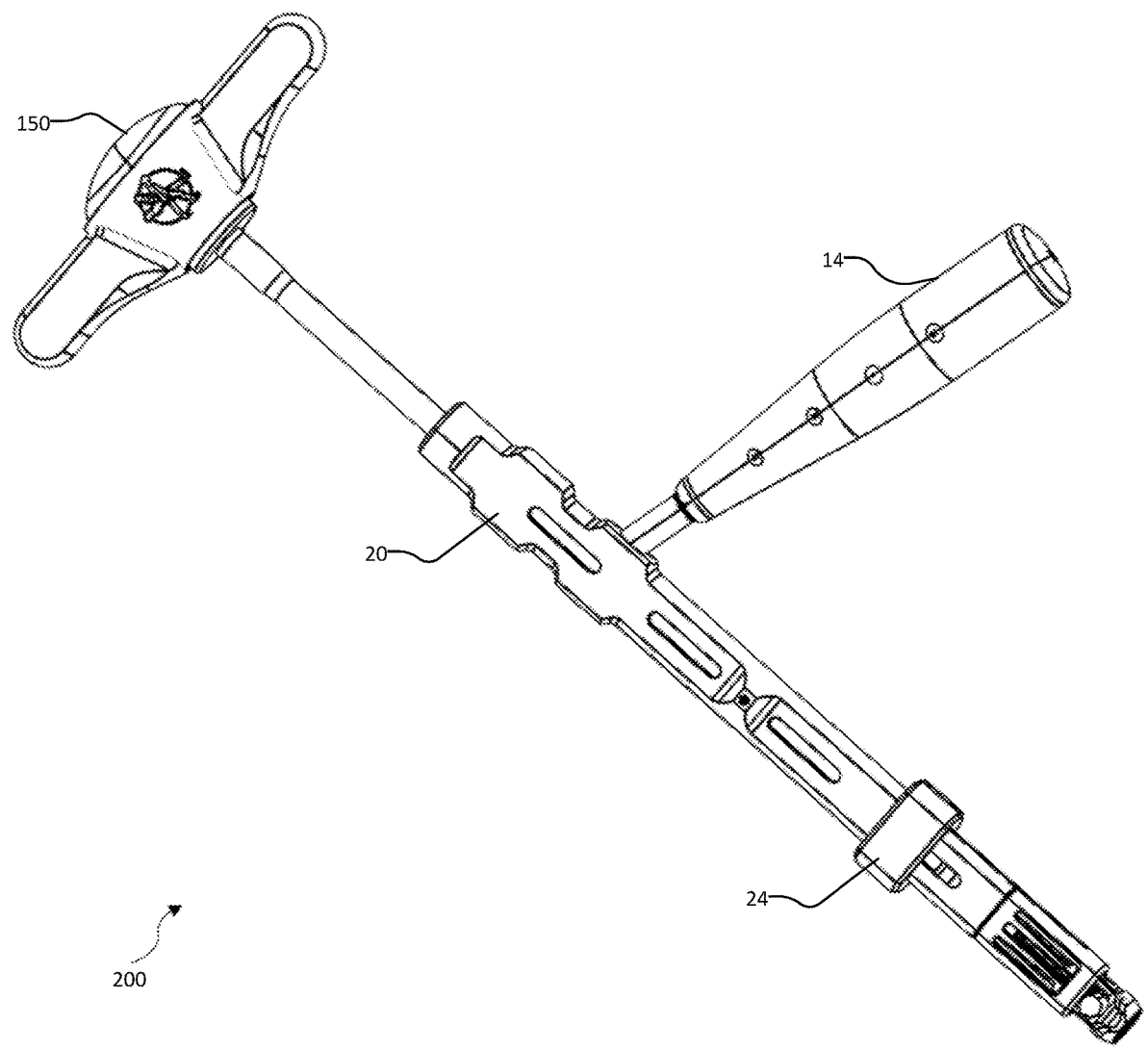
FIG. 12 is an example perspective view of a combination instrument including a collar for ejecting broken tabs of a reduction connector and a manual driver.
Figure 13:
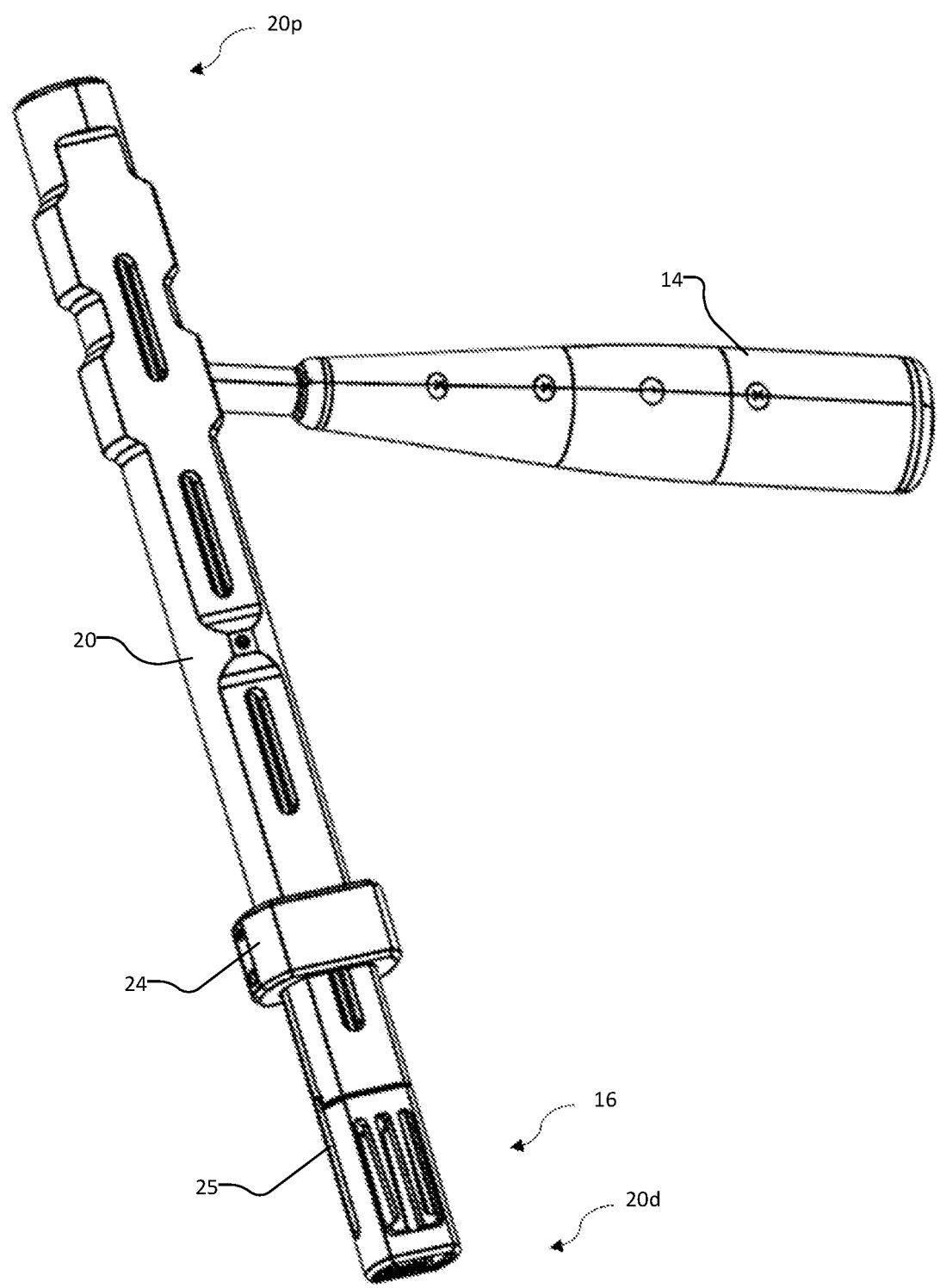
FIG. 13 is an example perspective view of a combination instrument including a collar for ejecting broken tabs of a reduction connector.
Figure 14:
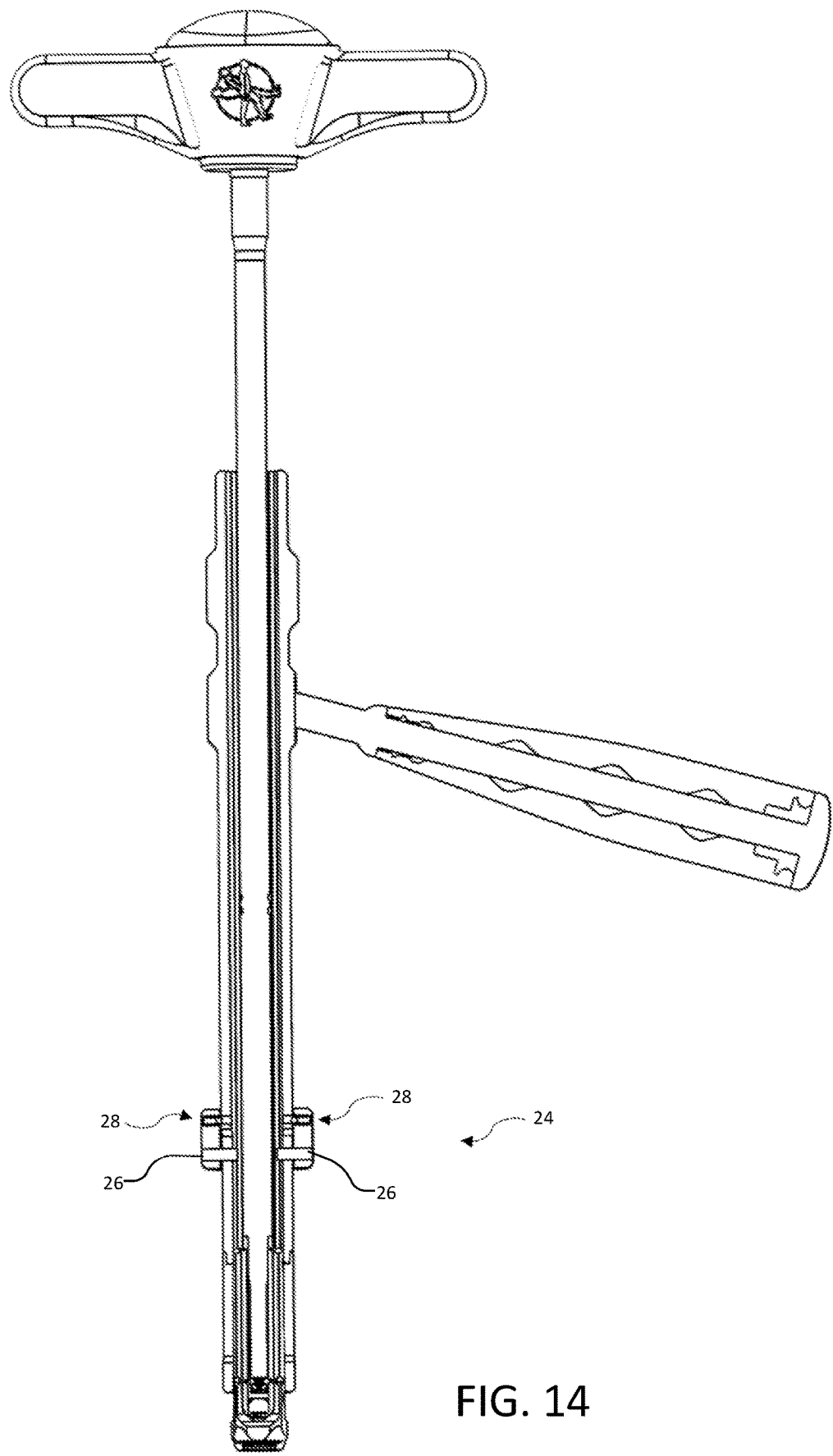
FIG. 14 is an example cross section view of a combination instrument including a collar for ejecting broken tabs of a reduction connector and a manual driver.
Figure 15:
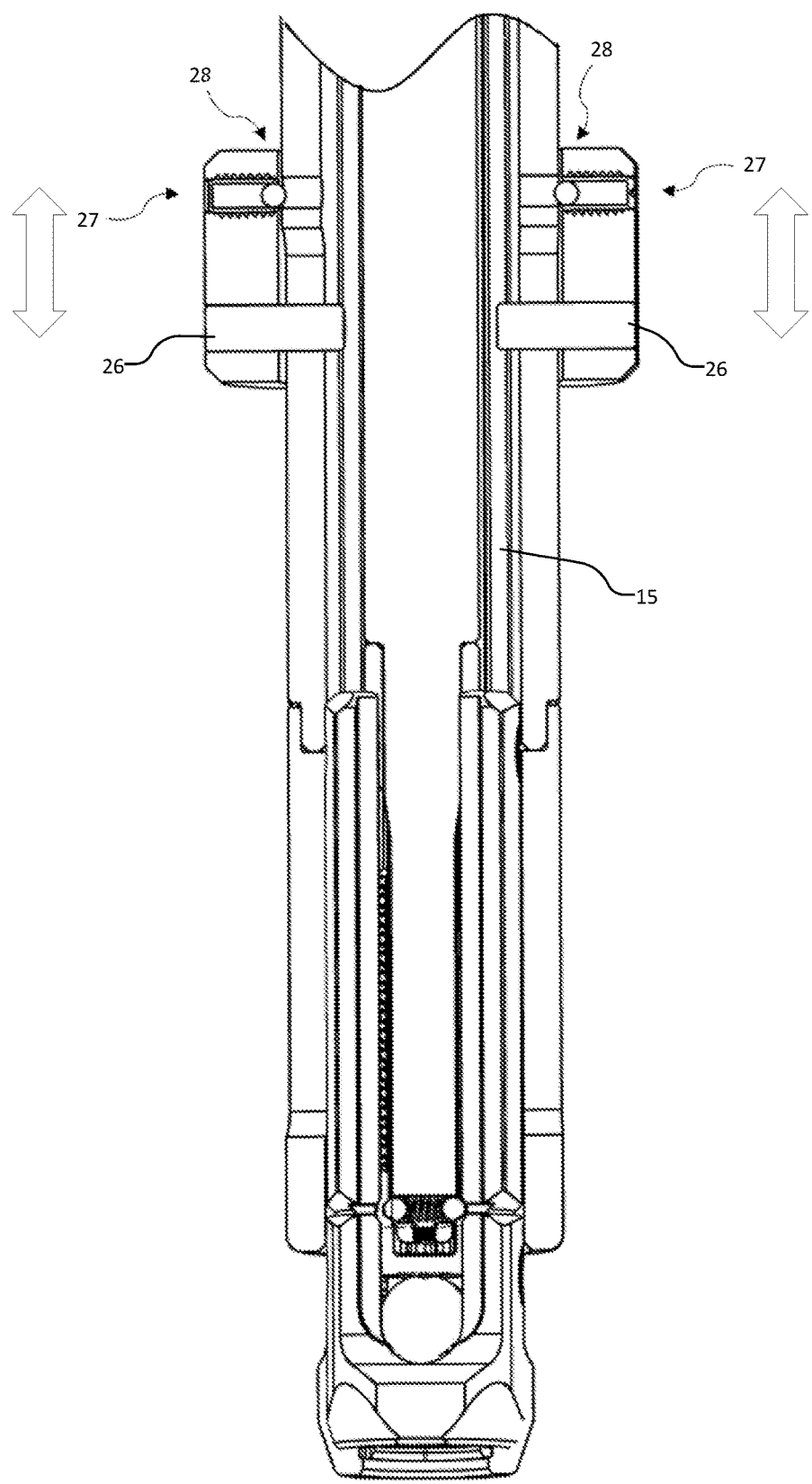
FIG. 15 is an example cross section view of a combination instrument including a collar for ejecting broken tabs of a reduction connector and a manual driver.

Referring generally to FIGS. 12-15, a surgery system 200 including a combination instrument 20 and a manual driver 150 is disclosed. FIG. 12 is an example perspective view of a combination instrument 20 including a collar 24 for ejecting broken tabs 3c and 3d of a reduction connector 3, for example. FIG. 13 is an example perspective view of a combination instrument 20 without a manual driver 150. FIG. 14 is an example cross section view of a combination instrument 20 including a collar 24 and a manual driver 150. FIG. 15 is an example cross section view of a combination instrument 20 including a collar 24 and a manual driver 150 seated on a reduction connector 3.

Combination instrument 20 may include the same, substantially the same, and/or similar components and functionality as combination instrument 10, for example. However, combination instrument 20 may differ from combination instrument 10 in that it includes a collar 24. Collar 24 may be configured to slide up and down combination instrument 20 towards and away from proximal end 20p and distal end 20d. For example, collar 24 may include a pair of cross pins 26 that extend laterally towards the interior shaft of combination instrument 20 such that each cross pin 26 extends through a corresponding channel 25. For example, each corresponding channel 25 may having a size and shape corresponding to geometry of the cross pins 26 for mating with the cross pins 26, respectively, such that the collar 24 may freely slide up and down the combination instrument 20 with the cross pins 26 extending into the magazine portion 15 for ejecting broken off tabs 3c and 3d stored therein. Collar 24 may further include a spring 27 biasing a ball 28 against an outside surface of combination instrument 20. In some embodiments, combination instrument 20 may include an indent adjacent a medial portion of combination instrument 20 such that collar 24 may be engaged in a storage location. For example, springs 27 may urge balls 28 into corresponding indents having a size and shape corresponding to geometry of the balls 28 for mating with the balls 28 such that collar 24 is fixed in a temporary storage location. A surgeon may apply a downward force against collar 24 and unseat balls 28 from their corresponding indents and freely slide collar 24 up and down combination instrument 20.

As explained above with respect to combination instrument 10, after tabs 3c and 3d are broken off they may be retained within magazine portion 15 and prevented from falling out due to cut-out portion 16. Collar 24 may be used to eject broken tabs 3c and 3d out of distal end 20d of combination instrument. In practice, a surgeon may break of tabs 3c and 3d as explained above with respect to combination instrument 10. Once the magazine portion 15 is stacked with broken tabs 3c and 3d a surgeon may slide collar 24 in a distal direction (represented schematically by arrows) such that cross pins 26 apply a downward force to the broken tabs 3c, 3d. The sliding down of collar 24 may exert enough force against tabs 3c and 3d to overcome the retaining force of cut-out portion 16. For example, the broken tabs 3c and 3d may be ejected from the combination instrument 20 due to cut-out portion 16 flexing outward and allowing broken tabs 3c and 3d to pass therethrough due to an applied force from collar 24. For example still, ribs or struts of the cut-out portion 16 that from a distal end 20d towards a proximal end 20p and are vertically aligned with rails of magazine portion 15 to retain the broken tabs 3c and 3d may be configured to bow or flex outwards when a sufficient downward force is applied by collar 24.

Figure 16:
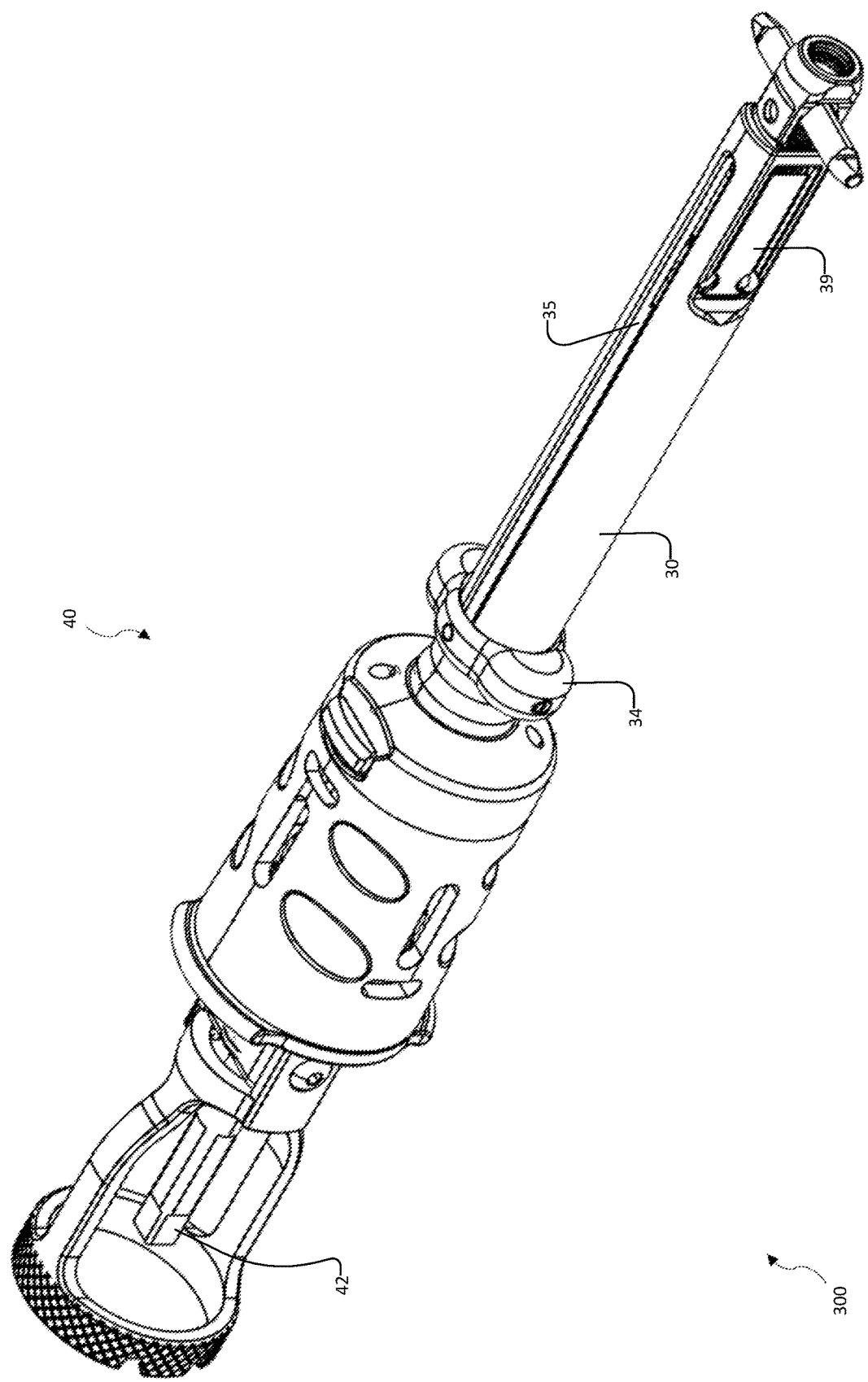
FIG. 16 is an example perspective view of a combination instrument for use with a powered driver.
Figure 17:
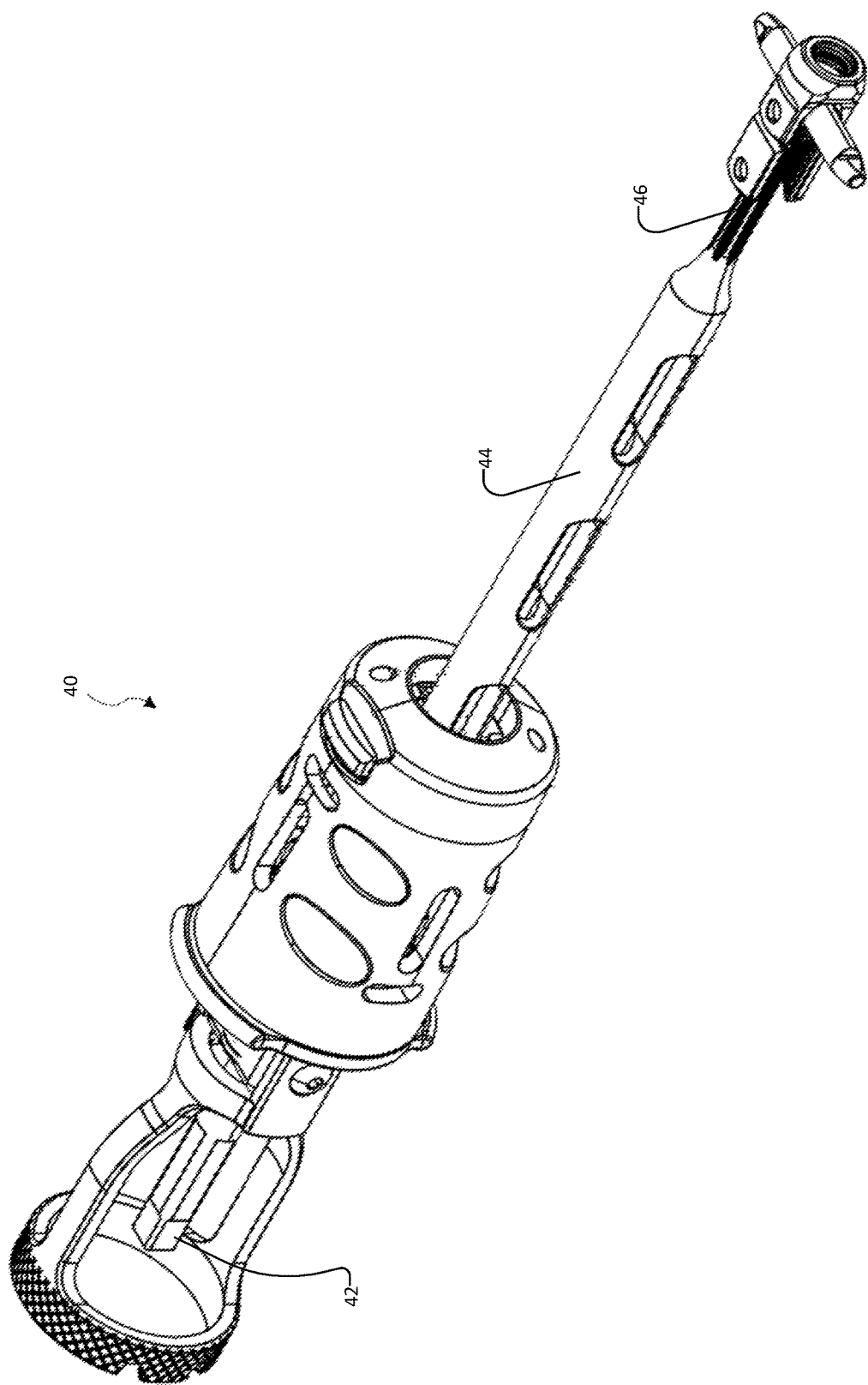
FIG. 17 is an example perspective view of a powered driver with some parts of an example combination instrument removed for ease of understanding.
Figure 18:
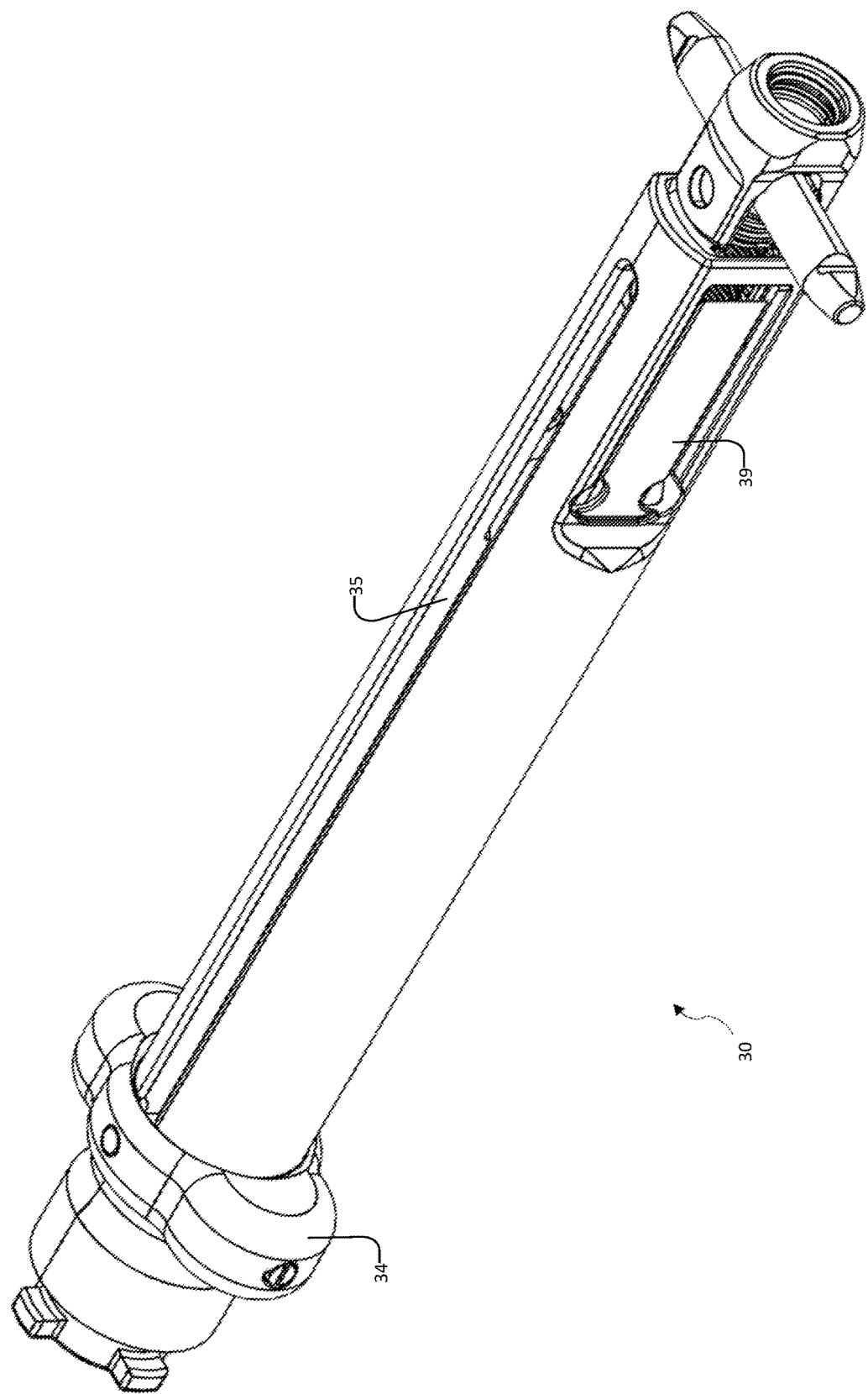
FIG. 18 is an example perspective view of a combination instrument for use with a powered driver.
Figure 19:
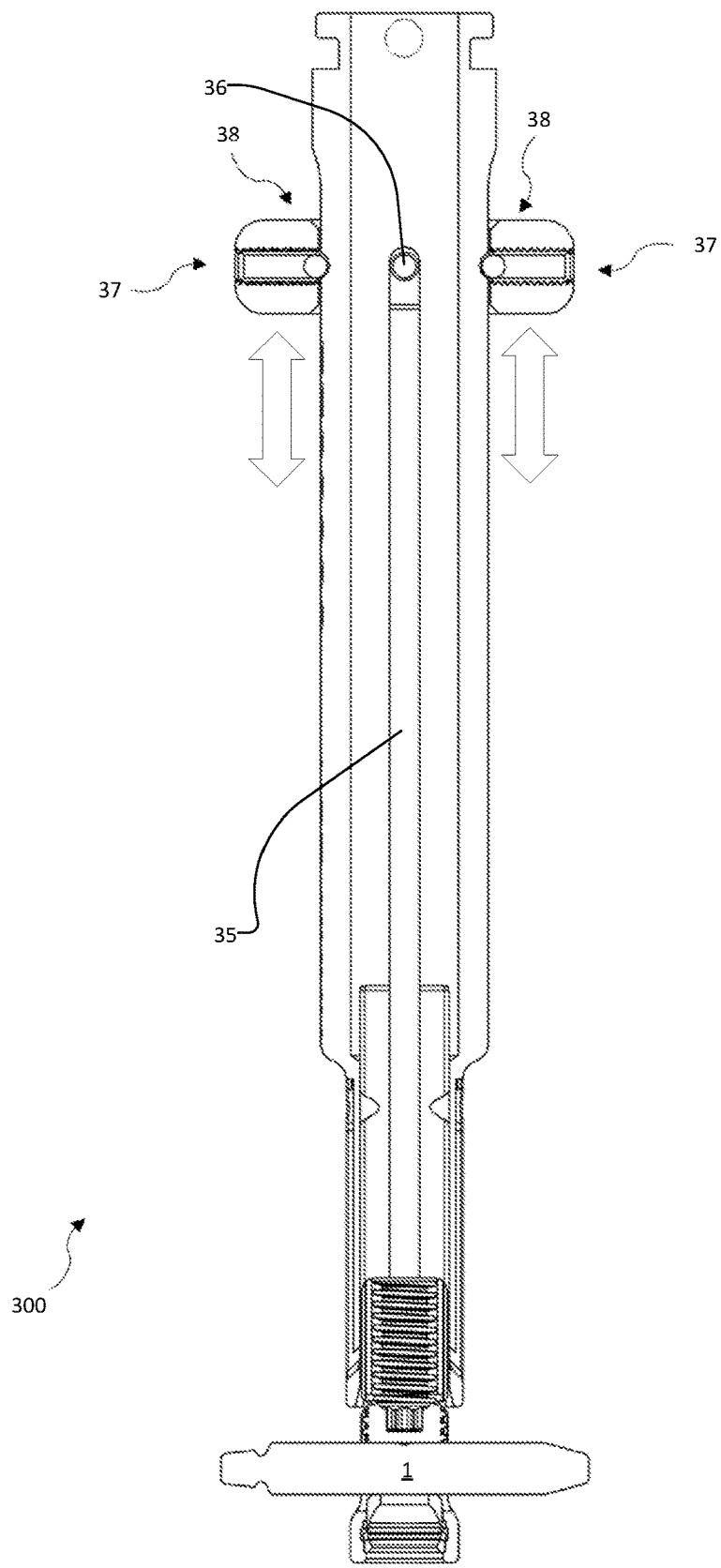
FIG. 19 is an example cross section view of a combination instrument for use with a powered driver.
Figure 20:
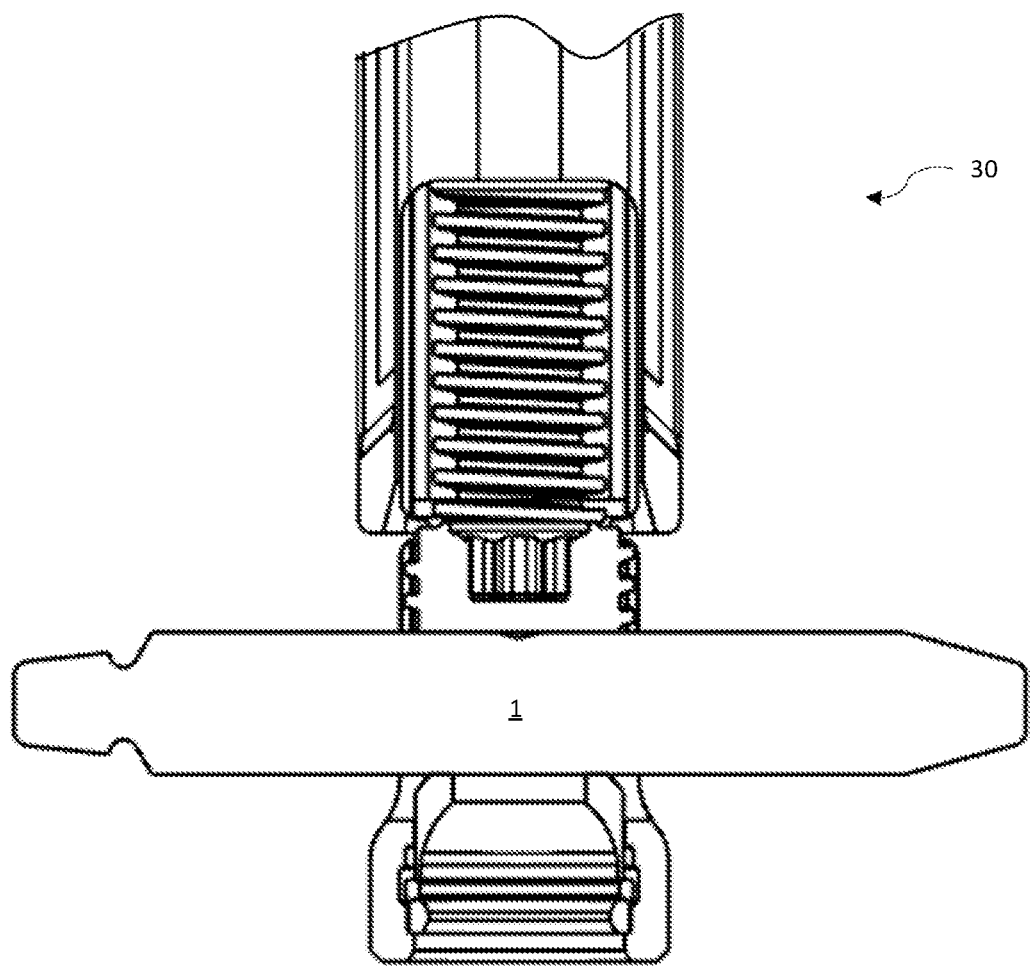
FIG. 20 is an example cross section view of a combination instrument for use with a powered driver.

Referring generally to FIGS. 16-22, a surgery system 300 including a combination instrument 30 and a powered driver 40 is disclosed. Powered driver 40 may include a drive end 42 that is configured to be powered by an external driver, such as, for example, Medtronic's PowerEase instruments or the like. FIG. 16 is an example perspective view of a combination instrument 30, and FIG. 17 is an example perspective view of a powered driver 40 without combination instrument 30. FIG. 18 is an example perspective view of a combination instrument 30 and FIG. 19 is an example cross section view of a combination instrument 30. Combination instrument 30 may include the same, substantially the same, or similar functionality and components as combination instruments 10 and 20 disclosed above. Combination instrument 30 may differ in that it is configured for use with a powered driver 40, for example. Although the example embodiments illustrate combination instrument 30 with a collar 34 other embodiments may be configured with a cap (not illustrated) that functions in the same, substantially the same, or similar manner as explained above with respect to cap 12 of combination instrument 10.

Combination instrument 30 may include a magazine portion for storage of broken off tabs 3c and 3d similarly as explained above. The broken off tabs 3c and 3d may be retained within the magazine portion in a space between drive shaft 44 and the surrounding internal surfaces of combination instrument 30, for example Broken off tabs 3c and 3d may be prevented from falling out of distal end 30d of combination instrument 30 due to cut-out portion 39. For example, cut-out portion 39 is inset from external side surfaces of combination instrument 30 and sized appropriately to keep broken off tabs 3c and 3d within the magazine portion of combination instrument 30 until collar 34 pushes the broken off tabs 3c and 3d out of the magazine portion.

Collar 34 may be configured to slide up and down combination instrument 30 towards and away from proximal end 30p and distal end 30d. For example, collar 34 may include a pair of cross pins 36 that extend laterally towards the interior shaft of combination instrument 30 such that each cross pin 36 extends through a corresponding channel 35. Collar 34 may further include a spring 37 biasing a ball 38 against an outside surface of combination instrument 30. In some embodiments, combination instrument 30 may include an indent adjacent a medial portion of combination instrument 30 such that collar 34 may be engaged in a storage location. For example, springs 37 may urge balls 38 into corresponding indents such that collar 34 is fixed in a temporary storage location. A surgeon may apply a downward force against collar 34 and unseat balls 38 from their corresponding indents and freely slide collar 34 up and down combination instrument 30, for example.

As explained above, collar 34 may be used to eject broken tabs 3c and 3d out of distal end 30d of combination instrument 30. In practice, a surgeon may break of tabs 3c and 3d as explained above with respect to combination instruments 10 and 20. Once the magazine portion is stacked with broken tabs 3c and 3d a surgeon may slide collar 34 in a distal direction such that cross pins 36 apply a downward force to the broken tabs 3c and 3d. The sliding down of collar 34 may exert enough force against tabs 3c and 3d to overcome the retaining force of cut-out portion 39. For example, in some embodiments the broken tabs 3c and 3d may be ejected from the combination instrument 20 due to cut-out portion 16 flexing outward and allowing broken tabs 3c and 3d to pass through due to an applied force from collar 34.

Figure 21:
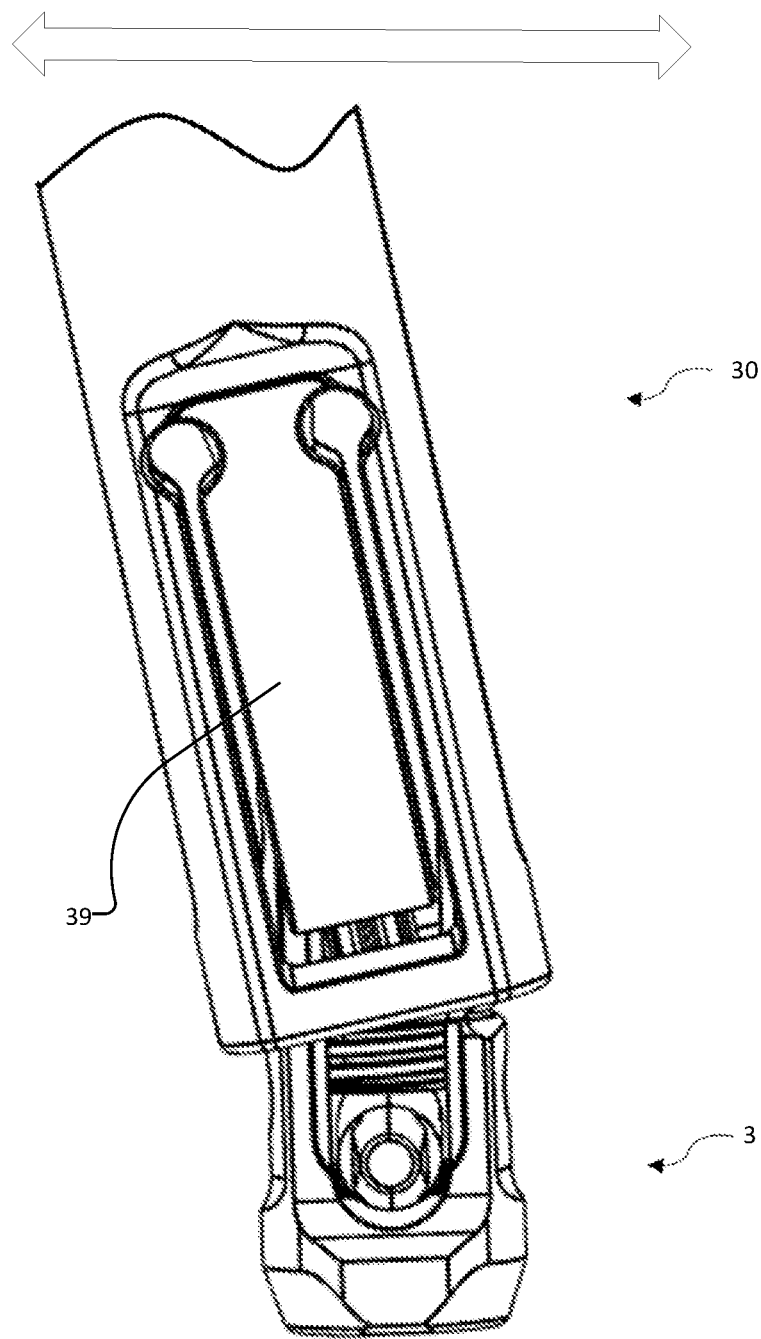
FIG. 21 is an example perspective view of a combination instrument being moved laterally with respect to a reduction connector to break off the tabs of the reduction connector.
Figure 22:
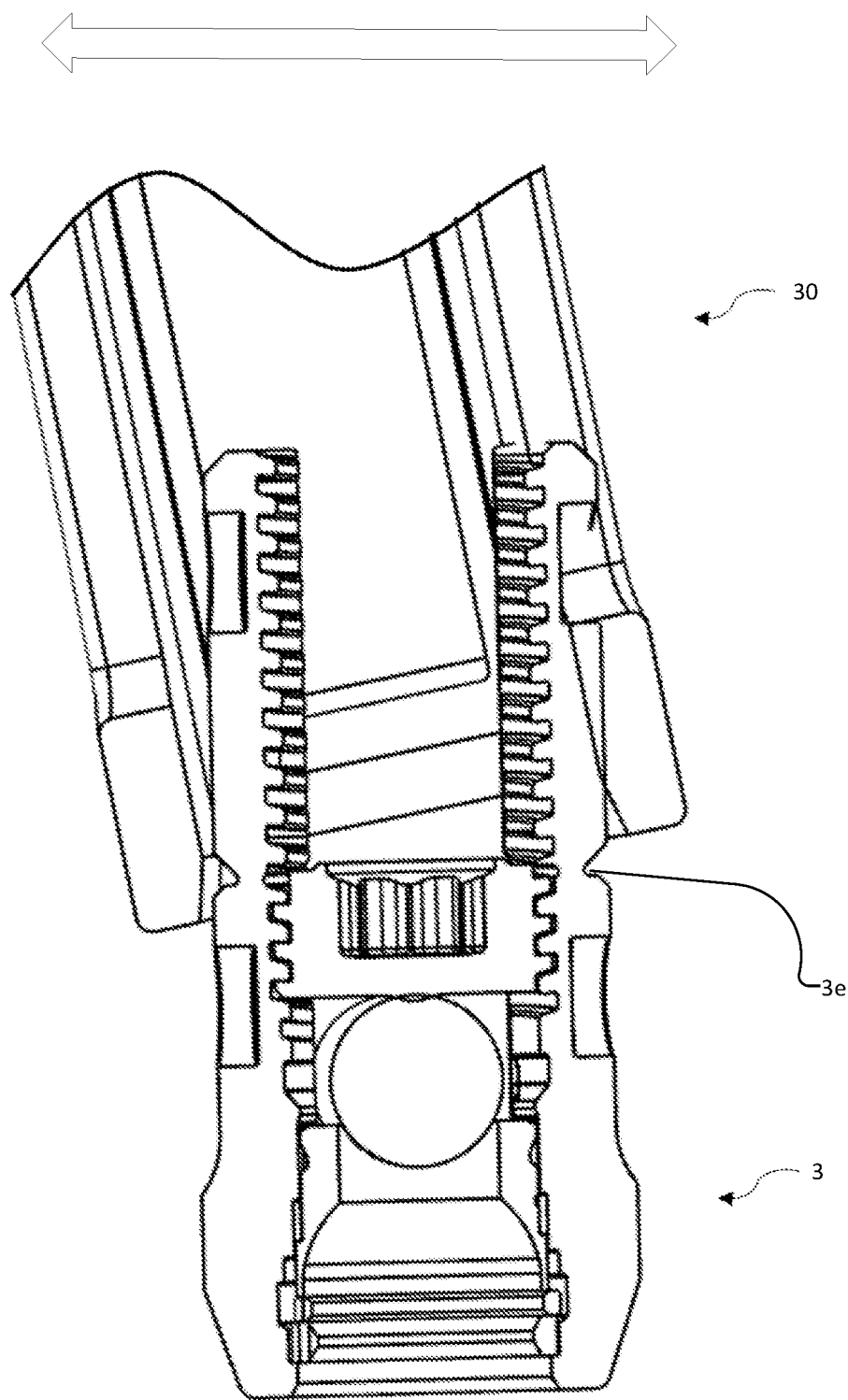
FIG. 22 is an example cross section view of a combination instrument being moved laterally with respect to a reduction connector to break off the tabs of the reduction connector.

FIG. 21 is an example perspective view of a combination instrument 30 being moved laterally with respect to a reduction connector 3 to break off the tabs 3c and 3d of the reduction connector 3. FIG. 22 is an example cross section view of a combination instrument 30 being moved laterally with respect to a reduction connector 3 to break off the tabs 3c and 3d of the reduction connector 3. Consistent with the disclosure herein, a surgeon may position combination instrument 30 such that a tip portion of distal end 30d is at the same elevation as the breakoff portion 3e of reduction connector 3. Thereafter, a surgeon may rock combination instrument 30 side to side from a medial position laterally to shear off the tabs 3c and 3d (represented schematically by arrows), for example. The tabs 3c and 3d may be retained within combination instrument 30 until such a time the surgeon decides to eject tabs 3c and 3d by way of collar 34 as explained above. In some embodiments, a surgeon may uncouple combination instrument 30 from driver 40 and pour out the broken tabs 3c and 3d from a proximal end 30p. For example, the broken tabs 3c and 3d may be stored or retained, at least temporarily, in a magazine portion having rails to stack the broken tabs 3c and 3d or within a cavity between drive shaft 44 and the internal sidewalls of combination instrument 30, for example. Alternatively, the tabs 3c and 3d may be retained within combination instrument 30 until such a time the surgeon decides to eject tabs 3c and 3d from a proximal end 30p by, for example, opening a cap (not illustrated) similar to cap 12 of combination instrument 10 and ejecting the broken off tabs 3c and 3d through an opening created by opening the cap.

The features and functions described above, as well as alternatives, may be combined into many other different systems or applications. Various alternatives, modifications, variations or improvements may be made by those skilled in the art, each of which is also intended to be encompassed by the disclosed embodiments.

What is claimed is:

1. A surgical system, comprising:
    a combination instrument having an elongated rigid structure extending from a proximal end to a distal end, the combination instrument including:
        a centrally disposed internal shaft extending from the proximal end to the distal end;
        a magazine portion surrounding at least some of the internal shaft, the magazine portion being configured to selectively store a plurality of broken off tabs of a reduction connector;
        a cap disposed at the proximal end, the cap being configured to retain the plurality of broken off tabs within the magazine portion at the proximal end such that when the cap is removed the plurality of broken off tabs may exit the magazine portion at the proximal end;
        a cut-out portion disposed at the distal end, the cut-out portion being configured to retain the at least one tab within the magazine portion at the distal end; and
        a driver configured to be selectively inserted through an aperture in the cap and into the internal shaft of the combination instrument and selectively removed from the internal shaft of the combination instrument,
        wherein the distal end of the combination instrument is configured to surround a reduction connector for breaking off tabs of the reduction connector in operation of the system, and
        wherein the driver is rotatable within the internal shaft of the combination instrument and includes a drive interface configured to drive a set screw generally corresponding in size and shape to a size and shape of the drive interface for mating with the drive interface.

2. The surgical system of claim 1, comprising:
    a handle positioned on a side surface of the combination instrument, the handle being configured to provide a counter torque to the reduction connector when driving the set screw in operation of the system.

3. The surgical system of claim 1, wherein the driver is configured to be driven by a powered device.

4. A surgical system, comprising:
    a combination instrument having an elongated rigid structure extending from a proximal end to a distal end, the combination instrument including:
        a centrally disposed internal shaft extending from the proximal end to the distal end;
        a magazine portion surrounding at least some of the internal shaft, the magazine portion being configured to selectively store at least one broken off tab of a reduction connector;
        a cut-out portion disposed at the distal end, the cut-out portion being configured to retain the at least one tab within the magazine portion at the distal end; and
        a driver configured to be selectively inserted into the internal shaft of the combination instrument and selectively removed from the internal shaft of the combination instrument,
        wherein the distal end of the combination instrument is configured to surround a reduction connector for breaking off tabs of the reduction connector in operation of the system,
    wherein the driver is rotatable within the internal shaft of the combination instrument and includes a drive interface configured to drive a set screw generally corresponding in size and shape to a size and shape of the drive interface for mating with the drive interface, and
    wherein the driver comprises at least one ball coupled to a corresponding biasing spring disposed on a drive portion of the driver, the at least one ball and corresponding biasing spring being configured to apply a lateral force, relative to the drive portion, against internal sidewalls of a head portion of the set screw.

5. The surgical system of claim 4, wherein:
the set screw is a breakoff set screw,
the driver is configured to break off a breakoff portion of a set screw, and
the at least one ball and corresponding biasing spring are configured to retain the breakoff portion of the breakoff set screw.

6. The surgical system of claim 4, wherein the driver is configured to be driven by a powered device.

7. A surgical system, comprising:
a combination instrument having an elongated rigid structure extending from a proximal end to a distal end, the combination instrument including:
a centrally disposed internal shaft extending from the proximal end to the distal end;
a magazine portion surrounding at least some of the internal shaft, the magazine portion being configured to selectively store at least one broken off tab of a reduction connector;
a cut-out portion disposed at the distal end, the cut-out portion being configured to retain the at least one tab within the magazine portion at the distal end;
a collar having at least two pins extending through corresponding channels of the combination instrument into the magazine portion, the corresponding channels having a size and shape corresponding to a size and shape of the at least two pins for mating with the at least two pins, respectively;
the collar being configured to slide along an outside surface of the combination instrument towards the distal end of the combination instrument to selectively eject the at least one tab stored in the magazine portion from the distal end of the combination instrument; and
a driver configured to be selectively inserted into the internal shaft of the combination instrument and selectively removed from the internal shaft of the combination instrument,
wherein the distal end of the combination instrument is configured to surround a reduction connector for breaking off tabs of the reduction connector in operation of the system, and
wherein the driver is rotatable within the internal shaft of the combination instrument and includes a drive interface configured to drive a set screw generally corresponding in size and shape to a size and shape of the drive interface for mating with the drive interface.

8. The surgical system of claim 7, wherein the driver is configured to be driven by a powered device.

* * * * *